(12) United States Patent
Albert

(10) Patent No.: US 10,537,250 B2
(45) Date of Patent: Jan. 21, 2020

(54) DISCORDANCE MONITORING

(71) Applicant: AliveCor, Inc., San Francisco, CA (US)

(72) Inventor: David E. Albert, Oklahoma City, OK (US)

(73) Assignee: AliveCor, Inc., Mountain View, CA (US)

( * ) Notice: Subject to any disclaimer, the term of this patent is extended or adjusted under 35 U.S.C. 154(b) by 0 days.

(21) Appl. No.: 15/656,745

(22) Filed: Jul. 21, 2017

(65) Prior Publication Data

US 2017/0319080 A1 Nov. 9, 2017

Related U.S. Application Data

(63) Continuation of application No. 15/154,849, filed on May 13, 2016.

(60) Provisional application No. 62/161,092, filed on May 13, 2015.

(51) Int. Cl.
| | |
|---|---|
| *A61B 5/02* | (2006.01) |
| *A61B 5/0205* | (2006.01) |
| *A61B 5/00* | (2006.01) |
| *A61B 5/024* | (2006.01) |
| *A61B 5/11* | (2006.01) |
| *A61B 5/046* | (2006.01) |
| *A61B 5/0464* | (2006.01) |
| *A61B 5/0408* | (2006.01) |

(52) U.S. Cl.
CPC ............ *A61B 5/0205* (2013.01); *A61B 5/681* (2013.01); *A61B 5/7267* (2013.01); *A61B 5/02405* (2013.01); *A61B 5/02438* (2013.01); *A61B 5/046* (2013.01); *A61B 5/0464* (2013.01); *A61B 5/04085* (2013.01); *A61B 5/1118* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 3,717,857 | A | 2/1973 | Evans |
| 3,731,311 | A | 5/1973 | Williams |
| 3,768,014 | A | 10/1973 | Smith et al. |
| 3,776,228 | A | 12/1973 | Semler |

(Continued)

FOREIGN PATENT DOCUMENTS

| | | |
|---|---|---|
| CH | 675675 A5 | 10/1990 |
| CN | 101828915 A | 9/2010 |

(Continued)

OTHER PUBLICATIONS

Adidas miCoach Pacer Review: Like Nike+, Only Better; printed from website: http://gizmodo.com/5479456/adidas• printed on Mar. 4, 2010, 5 pages.

(Continued)

*Primary Examiner* — Ankit D Tejani
(74) *Attorney, Agent, or Firm* — Womble Bond Dickinson (US) LLP; William D. Jacobs, Jr.

(57) ABSTRACT

Described herein are systems, devices, and methods for cardiac monitoring. In particular, the systems, devices, and methods described herein may be used to conveniently sense the presence of an intermittent arrhythmia in an individual. The systems, devices, and methods described herein may be further configured to sense an electrocardiogram.

16 Claims, 7 Drawing Sheets

(56) References Cited

U.S. PATENT DOCUMENTS

| | | |
|---|---|---|
| 3,779,237 A | 12/1973 | Roth et al. |
| 3,779,249 A | 12/1973 | Semler |
| 3,782,367 A | 1/1974 | Hochberg et al. |
| 3,805,227 A | 4/1974 | Lester |
| 3,882,277 A | 5/1975 | Depedro et al. |
| 3,885,552 A | 5/1975 | Kennedy |
| 3,898,984 A | 8/1975 | Mandel et al. |
| 3,909,599 A | 9/1975 | Trott, Jr. et al. |
| 4,027,146 A | 5/1977 | Gilmore |
| 4,045,767 A | 8/1977 | Nishihara et al. |
| 4,083,366 A | 4/1978 | Gombrich et al. |
| 4,095,050 A | 6/1978 | Beachem et al. |
| 4,221,223 A | 9/1980 | Linden |
| 4,230,127 A | 10/1980 | Larson |
| 4,231,031 A | 10/1980 | Crowther et al. |
| 4,250,888 A | 2/1981 | Grosskopf |
| 4,281,664 A | 8/1981 | Duggan |
| 4,295,472 A | 10/1981 | Adams |
| 4,312,358 A | 1/1982 | Barney |
| 4,318,130 A | 3/1982 | Heuer |
| 4,364,397 A | 12/1982 | Citron et al. |
| 4,367,752 A | 1/1983 | Jimenez et al. |
| 4,409,984 A | 10/1983 | Dick |
| 4,531,527 A | 7/1985 | Reinhold, Jr. et al. |
| 4,567,883 A | 2/1986 | Langer et al. |
| 4,572,182 A | 2/1986 | Royse |
| 4,580,250 A | 4/1986 | Kago et al. |
| 4,583,553 A | 4/1986 | Shah et al. |
| 4,622,979 A | 11/1986 | Katchis et al. |
| 4,625,730 A | 12/1986 | Fountain et al. |
| 4,803,625 A | 2/1989 | Fu et al. |
| 4,889,131 A | 12/1989 | Salem et al. |
| 4,920,489 A | 4/1990 | Hubelbank et al. |
| 4,938,228 A | 7/1990 | Righter et al. |
| 4,938,229 A | 7/1990 | Bergelson et al. |
| 4,958,641 A | 9/1990 | Digby et al. |
| 4,977,899 A | 12/1990 | Digby et al. |
| 4,981,141 A | 1/1991 | Segalowitz |
| 5,012,814 A | 5/1991 | Mills et al. |
| 5,023,906 A | 6/1991 | Novas |
| 5,025,794 A | 6/1991 | Albert et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,136,555 A | 8/1992 | Gardos |
| 5,181,552 A | 1/1993 | Eiermann |
| 5,191,891 A | 3/1993 | Righter |
| 5,201,321 A | 4/1993 | Fulton |
| 5,218,969 A | 6/1993 | Bredesen et al. |
| 5,226,424 A | 7/1993 | Bible |
| 5,238,001 A | 8/1993 | Gallant et al. |
| D341,659 S | 11/1993 | Homayoun |
| 5,259,387 A | 11/1993 | Depinto |
| 5,301,679 A | 4/1994 | Taylor |
| 5,304,186 A | 4/1994 | Semler et al. |
| 5,313,953 A | 5/1994 | Yomtov et al. |
| 5,321,618 A | 6/1994 | Gessman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,360,005 A | 11/1994 | Wilk |
| 5,365,935 A | 11/1994 | Righter et al. |
| 5,410,587 A | 4/1995 | Grunwell |
| 5,417,222 A | 5/1995 | Dempsey et al. |
| 5,433,736 A | 7/1995 | Nilsson |
| 5,452,356 A | 9/1995 | Albert |
| 5,466,246 A | 11/1995 | Silvian |
| 5,467,773 A | 11/1995 | Bergelson et al. |
| 5,481,255 A | 1/1996 | Albert et al. |
| 5,503,158 A | 4/1996 | Coppock et al. |
| 5,518,001 A | 5/1996 | Snell |
| 5,522,396 A | 6/1996 | Langer et al. |
| 5,539,705 A | 7/1996 | Akerman et al. |
| D372,785 S | 8/1996 | Sabri |
| 5,544,661 A | 8/1996 | Davis et al. |
| 5,551,953 A | 9/1996 | Lattin et al. |
| 5,561,712 A | 10/1996 | Nishihara |
| 5,568,448 A | 10/1996 | Tanigushi et al. |
| 5,579,284 A | 11/1996 | May |
| D377,983 S | 2/1997 | Sabri |
| 5,608,723 A | 3/1997 | Felsenstein |
| 5,634,468 A | 6/1997 | Platt et al. |
| 5,652,570 A | 7/1997 | Lepkofker |
| 5,661,699 A | 8/1997 | Sutton |
| 5,675,325 A | 10/1997 | Taniguchi et al. |
| 5,678,562 A | 10/1997 | Sellers |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,735,285 A | 4/1998 | Albert et al. |
| 5,742,251 A | 4/1998 | Gerber |
| 5,748,103 A | 5/1998 | Flach et al. |
| 5,764,763 A | 6/1998 | Jensen et al. |
| 5,772,586 A | 6/1998 | Heinonen et al. |
| 5,818,788 A | 10/1998 | Kimura et al. |
| 5,825,718 A | 10/1998 | Ueki et al. |
| 5,827,179 A | 10/1998 | Lichter et al. |
| 5,840,020 A | 11/1998 | Heinonen et al. |
| 5,844,997 A | 12/1998 | Murphy, Jr. |
| 5,861,018 A | 1/1999 | Feierbach |
| 5,873,369 A | 2/1999 | Laniado et al. |
| 5,876,351 A | 3/1999 | Rohde |
| 5,877,675 A | 3/1999 | Rebstock et al. |
| 5,889,730 A | 3/1999 | May |
| 5,929,761 A | 7/1999 | Van et al. |
| D414,870 S | 10/1999 | Saltzstein |
| 5,970,388 A | 10/1999 | Will |
| 5,976,083 A | 11/1999 | Richardson et al. |
| 5,982,297 A | 11/1999 | Welle |
| 5,983,127 A | 11/1999 | Depinto |
| 6,008,703 A | 12/1999 | Perrott et al. |
| 6,024,705 A | 2/2000 | Schlager et al. |
| 6,037,704 A | 3/2000 | Welle |
| 6,047,257 A | 4/2000 | Dewaele |
| 6,048,319 A | 4/2000 | Hudgins et al. |
| D427,315 S | 6/2000 | Saltzstein |
| 6,072,396 A | 6/2000 | Gaukel |
| 6,083,248 A | 7/2000 | Thompson |
| 6,084,510 A | 7/2000 | Lemelson et al. |
| 6,102,856 A | 8/2000 | Groff et al. |
| 6,153,532 A | 11/2000 | Dow et al. |
| 6,159,147 A | 12/2000 | Lichter et al. |
| 6,198,394 B1 | 3/2001 | Jacobsen et al. |
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk |
| 6,343,049 B1 | 1/2002 | Toda |
| 6,363,139 B1 | 3/2002 | Zurek et al. |
| 6,364,834 B1 | 4/2002 | Reuss et al. |
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,478,736 B1 | 11/2002 | Mault |
| 6,485,416 B1 | 11/2002 | Platt et al. |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey, III et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |

(56) References Cited

U.S. PATENT DOCUMENTS

| | | | |
|---|---|---|---|
| 6,612,985 | B2 | 9/2003 | Eiffert et al. |
| 6,616,613 | B1 | 9/2003 | Goodman |
| 6,636,761 | B2 | 10/2003 | Brodnick |
| 6,685,633 | B2 | 2/2004 | Albert et al. |
| 6,717,983 | B1 | 4/2004 | Toda |
| 6,790,178 | B1 | 9/2004 | Mault et al. |
| 6,804,558 | B2 | 10/2004 | Haller et al. |
| 6,820,057 | B1 | 11/2004 | Loch et al. |
| 6,845,263 | B2 | 1/2005 | Kawaguchi |
| 6,893,396 | B2 | 5/2005 | Schulze et al. |
| 6,928,535 | B2 | 8/2005 | Yamashita et al. |
| 6,950,681 | B2 | 9/2005 | Hofmann |
| 6,970,737 | B1 | 11/2005 | Brodnick et al. |
| 6,987,965 | B2 | 1/2006 | Ng et al. |
| 7,018,339 | B2 | 3/2006 | Birnbaum et al. |
| 7,020,508 | B2 | 3/2006 | Stivoric et al. |
| 7,031,745 | B2 | 4/2006 | Shen |
| 7,061,381 | B2 | 6/2006 | Forcier et al. |
| 7,103,407 | B2 | 9/2006 | Hjelt et al. |
| 7,107,095 | B2 | 9/2006 | Manolas |
| 7,108,659 | B2 | 9/2006 | Ross et al. |
| 7,153,262 | B2 | 12/2006 | Stivoric et al. |
| 7,162,291 | B1 | 1/2007 | Nachaliel |
| 7,162,294 | B2 | 1/2007 | Rowlandson et al. |
| 7,188,151 | B2 | 3/2007 | Kumar et al. |
| 7,222,054 | B2 | 5/2007 | Geva |
| 7,236,818 | B2 | 6/2007 | McLeod et al. |
| 7,257,448 | B2 | 8/2007 | Crowe et al. |
| 7,260,429 | B2 | 8/2007 | Siejko et al. |
| 7,261,690 | B2 | 8/2007 | Teller et al. |
| 7,285,090 | B2 | 10/2007 | Stivoric et al. |
| 7,319,425 | B2 | 1/2008 | Fiorenza et al. |
| 7,324,836 | B2 | 1/2008 | Steenstra et al. |
| 7,349,574 | B1 | 3/2008 | Sodini et al. |
| 7,351,207 | B2 | 4/2008 | Priemer |
| 7,354,400 | B2 | 4/2008 | Asafusa et al. |
| 7,382,247 | B2 | 6/2008 | Welch et al. |
| 7,383,297 | B1 | 6/2008 | Atsmon et al. |
| 7,398,115 | B2 | 7/2008 | Lynn |
| 7,415,304 | B2 | 8/2008 | Rowlandson et al. |
| 7,444,116 | B2 | 10/2008 | Ivanov et al. |
| 7,460,899 | B2 | 12/2008 | Almen |
| 7,502,643 | B2 | 3/2009 | Farringdon et al. |
| 7,509,159 | B2 | 3/2009 | Xue et al. |
| 7,515,043 | B2 | 4/2009 | Welch et al. |
| 7,515,044 | B2 | 4/2009 | Welch et al. |
| 7,520,860 | B2 | 4/2009 | Guion-Johnson et al. |
| 7,542,878 | B2 | 6/2009 | Nanikashvili |
| 7,548,623 | B2 | 6/2009 | Manabe |
| 7,596,405 | B2 | 9/2009 | Kurzweil et al. |
| 7,603,148 | B2 | 10/2009 | Michalak |
| 7,647,185 | B2 | 1/2010 | Tarassenko et al. |
| 7,654,148 | B2 | 2/2010 | Tomlinson |
| 7,657,479 | B2 | 2/2010 | Henley |
| 7,668,589 | B2 | 2/2010 | Bauer |
| 7,689,437 | B1 | 3/2010 | Teller et al. |
| 7,701,895 | B2 | 4/2010 | Gehasie et al. |
| 7,733,224 | B2 | 6/2010 | Tran |
| 7,742,808 | B2 | 6/2010 | Nissila et al. |
| 7,806,832 | B2 | 10/2010 | Gallagher et al. |
| 7,819,814 | B2 | 10/2010 | Gavriely et al. |
| 7,846,104 | B2 | 12/2010 | MacQuarrie et al. |
| 7,846,106 | B2 | 12/2010 | Andrews |
| 7,904,160 | B2 | 3/2011 | Brodnick et al. |
| 7,945,064 | B2 | 5/2011 | O'Brien et al. |
| 7,946,959 | B2 | 5/2011 | Shum et al. |
| 7,955,273 | B2 | 6/2011 | Rahe-Meyer |
| 7,983,749 | B2 | 7/2011 | Warren |
| 8,019,609 | B2 | 9/2011 | Tamir et al. |
| 8,034,006 | B2 | 10/2011 | Celik-Butler et al. |
| 8,062,090 | B2 | 11/2011 | Atsmon et al. |
| 8,078,136 | B2 | 12/2011 | Atsmon et al. |
| 8,078,278 | B2 | 12/2011 | Penner |
| 8,126,526 | B2 | 2/2012 | Kitajima et al. |
| 8,126,566 | B2 | 2/2012 | Stahmann et al. |
| 8,126,728 | B2 | 2/2012 | Dicks et al. |
| 8,130,093 | B2 | 3/2012 | Mazar et al. |
| 8,150,750 | B2 | 4/2012 | Ray |
| 8,160,276 | B2 | 4/2012 | Liao et al. |
| 8,165,677 | B2 | 4/2012 | Von et al. |
| 8,216,136 | B2 | 7/2012 | Addison et al. |
| 8,224,429 | B2 | 7/2012 | Prstojevich et al. |
| 8,265,907 | B2 | 9/2012 | Nanikashvili et al. |
| 8,275,553 | B2 | 9/2012 | Ochs et al. |
| 8,275,635 | B2 | 9/2012 | Stivoric et al. |
| 8,282,550 | B2 | 10/2012 | Rasdal et al. |
| 8,285,356 | B2 | 10/2012 | Bly et al. |
| 8,301,232 | B2 | 10/2012 | Albert et al. |
| 8,301,236 | B2 | 10/2012 | Baumann et al. |
| 8,323,188 | B2 | 12/2012 | Tran |
| 8,328,718 | B2 | 12/2012 | Tran |
| 8,332,233 | B2 | 12/2012 | Ott et al. |
| 8,364,250 | B2 | 1/2013 | Moon et al. |
| 8,369,936 | B2 | 2/2013 | Farringdon et al. |
| 8,374,688 | B2 | 2/2013 | Libbus et al. |
| 8,449,471 | B2 | 5/2013 | Tran |
| 8,500,636 | B2 | 8/2013 | Tran |
| 8,509,882 | B2 | 8/2013 | Albert et al. |
| 8,519,835 | B2 | 8/2013 | Dunko |
| 8,543,185 | B2 | 9/2013 | Yuen et al. |
| 8,548,770 | B2 | 10/2013 | Yuen et al. |
| 8,700,137 | B2 | 4/2014 | Albert |
| 8,725,229 | B2 | 5/2014 | Furue et al. |
| 8,755,871 | B2 | 6/2014 | Weng et al. |
| 8,923,958 | B2 | 12/2014 | Gupta et al. |
| 8,951,189 | B2 | 2/2015 | Osorio |
| 8,951,192 | B2 | 2/2015 | Osorio |
| 8,974,396 | B1 | 3/2015 | Brady et al. |
| 8,977,347 | B2 | 3/2015 | Mestha et al. |
| 9,026,202 | B2 | 5/2015 | Albert |
| 9,220,430 | B2 | 12/2015 | Albert |
| 9,254,095 | B2 | 2/2016 | Galloway et al. |
| 9,351,654 | B2 | 5/2016 | Albert |
| 2001/0027384 | A1 | 10/2001 | Schulze et al. |
| 2001/0031998 | A1 | 10/2001 | Nelson et al. |
| 2001/0051766 | A1 | 12/2001 | Gazdzinski |
| 2002/0016541 | A1 | 2/2002 | Glossop |
| 2002/0032386 | A1 | 3/2002 | Sackner et al. |
| 2002/0111556 | A1 | 8/2002 | Wegner |
| 2002/0143576 | A1 | 10/2002 | Nolvak et al. |
| 2003/0004425 | A1 | 1/2003 | Narimatsu et al. |
| 2003/0093002 | A1 | 5/2003 | Kuo |
| 2003/0107487 | A1 | 6/2003 | Korman et al. |
| 2003/0117987 | A1 | 6/2003 | Brebner |
| 2003/0149344 | A1 | 8/2003 | Nizan |
| 2003/0193839 | A1 | 10/2003 | Singh |
| 2004/0034284 | A1 | 2/2004 | Aversano et al. |
| 2004/0044292 | A1 | 3/2004 | Yasushi et al. |
| 2004/0059205 | A1 | 3/2004 | Carlson et al. |
| 2004/0117212 | A1 | 6/2004 | Kong et al. |
| 2004/0120356 | A1 | 6/2004 | Davenport et al. |
| 2004/0143403 | A1 | 7/2004 | Brandon et al. |
| 2004/0215088 | A1 | 10/2004 | Hubelbank |
| 2004/0215094 | A1 | 10/2004 | Baumer et al. |
| 2004/0220487 | A1 | 11/2004 | Vyshedskiy et al. |
| 2004/0220488 | A1 | 11/2004 | Vyshedskiy et al. |
| 2004/0225199 | A1 | 11/2004 | Evanyk et al. |
| 2004/0228217 | A1 | 11/2004 | Szeto |
| 2004/0236819 | A1 | 11/2004 | Anati et al. |
| 2004/0266407 | A1 | 12/2004 | Lee et al. |
| 2004/0266480 | A1 | 12/2004 | Hjelt et al. |
| 2005/0014531 | A1 | 1/2005 | Findikli |
| 2005/0027207 | A1 | 2/2005 | Westbrook et al. |
| 2005/0078533 | A1 | 4/2005 | Vyshedskiy et al. |
| 2005/0124864 | A1 | 6/2005 | Mack et al. |
| 2005/0234353 | A1 | 10/2005 | Xue et al. |
| 2006/0022833 | A1 | 2/2006 | Ferguson et al. |
| 2006/0047215 | A1 | 3/2006 | Newman et al. |
| 2006/0173259 | A1 | 8/2006 | Flaherty et al. |
| 2006/0190045 | A1 | 8/2006 | Marcus et al. |
| 2006/0193270 | A1 | 8/2006 | Gehasie et al. |
| 2006/0252999 | A1 | 11/2006 | Devaul et al. |
| 2007/0021677 | A1 | 1/2007 | Markel |
| 2007/0027386 | A1 | 2/2007 | Such et al. |

(56) References Cited

U.S. PATENT DOCUMENTS

| | | |
|---|---|---|
| 2007/0032731 A1 | 2/2007 | Lovejoy et al. |
| 2007/0063850 A1 | 3/2007 | Devaul et al. |
| 2007/0073266 A1 | 3/2007 | Chmiel et al. |
| 2007/0106133 A1 | 5/2007 | Satchwell et al. |
| 2007/0106179 A1 | 5/2007 | Bagha et al. |
| 2007/0156060 A1 | 7/2007 | Cervantes et al. |
| 2007/0254604 A1 | 11/2007 | Kim |
| 2007/0265038 A1 | 11/2007 | Kim |
| 2008/0009759 A1 | 1/2008 | Chetham et al. |
| 2008/0058670 A1 | 3/2008 | Mainini |
| 2008/0112885 A1 | 5/2008 | Okunev et al. |
| 2008/0146890 A1 | 6/2008 | Leboeuf et al. |
| 2008/0171945 A1 | 7/2008 | Dotter |
| 2008/0177162 A1 | 7/2008 | Bae et al. |
| 2008/0198872 A1 | 8/2008 | Pierce |
| 2008/0214903 A1 | 9/2008 | Orbach |
| 2008/0228045 A1 | 9/2008 | Gao et al. |
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0306485 A1 | 12/2009 | Bell |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0035927 A1 | 2/2010 | Ojika et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0184479 A1 | 7/2010 | Griffin, Jr. |
| 2010/0204758 A1 | 8/2010 | Boon et al. |
| 2010/0208434 A1 | 8/2010 | Kim et al. |
| 2010/0217099 A1 | 8/2010 | Leboeuf et al. |
| 2010/0217100 A1 | 8/2010 | Leboeuf et al. |
| 2010/0217345 A1 | 8/2010 | Wolfe et al. |
| 2010/0234746 A1 | 9/2010 | Sebelius et al. |
| 2010/0256509 A1 | 10/2010 | Kuo et al. |
| 2010/0256976 A1 | 10/2010 | Atsmon et al. |
| 2010/0281261 A1 | 11/2010 | Razzell |
| 2010/0298711 A1 | 11/2010 | Pedersen et al. |
| 2010/0324378 A1 | 12/2010 | Tran et al. |
| 2010/0331631 A1 | 12/2010 | Maclaughlin |
| 2011/0015496 A1 | 1/2011 | Sherman et al. |
| 2011/0035927 A1 | 2/2011 | Griffin et al. |
| 2011/0060251 A1 | 3/2011 | Verma et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0160601 A1 | 6/2011 | Wang et al. |
| 2011/0182445 A1 | 7/2011 | Atsmon et al. |
| 2011/0208076 A1 | 8/2011 | Fong et al. |
| 2011/0235466 A1 | 9/2011 | Booij et al. |
| 2011/0275950 A1 | 11/2011 | Xue et al. |
| 2011/0288425 A1 | 11/2011 | Stewart |
| 2011/0301435 A1 | 12/2011 | Albert et al. |
| 2011/0301439 A1 | 12/2011 | Albert et al. |
| 2012/0051187 A1 | 3/2012 | Paulson et al. |
| 2012/0053424 A1 | 3/2012 | Kenalty et al. |
| 2012/0071734 A1 | 3/2012 | Shimuta et al. |
| 2012/0101396 A1 | 4/2012 | Solosko et al. |
| 2012/0108916 A1 | 5/2012 | Riftine |
| 2012/0109675 A1* | 5/2012 | Ziegler ................ G06Q 50/22 705/2 |
| 2012/0123891 A1 | 5/2012 | Patel |
| 2012/0127833 A1 | 5/2012 | Ghen et al. |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0158090 A1 | 6/2012 | Chavan et al. |
| 2012/0171963 A1 | 7/2012 | Tsfaty |
| 2012/0172689 A1 | 7/2012 | Albert et al. |
| 2012/0179056 A1 | 7/2012 | Moulder et al. |
| 2012/0197148 A1 | 8/2012 | Levitan et al. |
| 2012/0285588 A1 | 11/2012 | Sheppard |
| 2012/0289790 A1* | 11/2012 | Jain ................ A61B 5/4848 600/301 |
| 2012/0316413 A1 | 12/2012 | Liu et al. |
| 2013/0003852 A1 | 1/2013 | Yamamoto |
| 2013/0030259 A1 | 1/2013 | Thomsen et al. |
| 2013/0085364 A1 | 4/2013 | Lu et al. |
| 2013/0122810 A1 | 5/2013 | Kaufman |
| 2013/0156194 A1 | 6/2013 | Tanioka |
| 2013/0159699 A1 | 6/2013 | Torkkel |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0289366 A1 | 10/2013 | Chua et al. |
| 2013/0331663 A1 | 12/2013 | Albert et al. |
| 2014/0050321 A1 | 2/2014 | Albert et al. |
| 2014/0051941 A1 | 2/2014 | Messerschmidt |
| 2014/0051946 A1 | 2/2014 | Arne et al. |
| 2014/0066798 A1 | 3/2014 | Albert |
| 2014/0073969 A1 | 3/2014 | Zou et al. |
| 2014/0114166 A1 | 4/2014 | Baxi |
| 2014/0163393 A1* | 6/2014 | McCombie ........ G06F 19/3437 600/483 |
| 2014/0221859 A1 | 8/2014 | Albert |
| 2014/0276162 A1 | 9/2014 | Albert et al. |
| 2015/0018660 A1 | 1/2015 | Thomson et al. |
| 2015/0057512 A1* | 2/2015 | Kapoor ................ A61B 5/0205 600/324 |
| 2015/0087952 A1 | 3/2015 | Albert et al. |
| 2015/0126878 A1* | 5/2015 | An ................ A61B 5/01 600/484 |
| 2015/0182132 A1 | 7/2015 | Harris et al. |
| 2015/0265164 A1 | 9/2015 | Gopalakrishnan et al. |
| 2015/0297134 A1 | 10/2015 | Albert et al. |
| 2016/0071392 A1 | 3/2016 | Hankey et al. |

FOREIGN PATENT DOCUMENTS

| | | |
|---|---|---|
| CN | 201918016 U | 8/2011 |
| CN | 102347804 A | 2/2012 |
| CN | 105338892 A | 2/2016 |
| DE | 2506936 A1 | 9/1976 |
| DE | 4212670 A1 | 1/1994 |
| EP | 0631226 A1 | 12/1994 |
| EP | 1181888 B1 | 9/2007 |
| EP | 1238633 B1 | 10/2008 |
| EP | 2030565 A1 | 3/2009 |
| EP | 2116183 B1 | 2/2012 |
| EP | 2986204 A1 | 2/2016 |
| FR | 2740426 A1 | 4/1997 |
| GB | 2181554 A | 4/1987 |
| GB | 2408105 A | 5/2005 |
| JP | S59122032 A | 7/1984 |
| JP | S59190742 A | 10/1984 |
| JP | S63072231 A | 4/1988 |
| JP | S63294044 A | 11/1988 |
| JP | H01244328 A | 9/1989 |
| JP | H05167540 A | 7/1993 |
| JP | H06326669 A | 11/1994 |
| JP | 2002191562 A | 7/2002 |
| JP | 2002261731 A | 9/2002 |
| JP | 2003010177 A | 1/2003 |
| JP | 2005295378 A | 10/2005 |
| JP | 2012065073 A | 3/2012 |
| KR | 20100059198 A | 6/2010 |

(56) References Cited

FOREIGN PATENT DOCUMENTS

| | | |
|---|---|---|
| MX | 2009011781 A | 5/2011 |
| WO | WO-8200910 A1 | 3/1982 |
| WO | WO-8805282 A1 | 7/1988 |
| WO | WO-9008361 A1 | 7/1990 |
| WO | WO-9206551 A1 | 4/1992 |
| WO | WO-9731437 A1 | 8/1997 |
| WO | WO-9838611 A1 | 9/1998 |
| WO | WO-9944494 A1 | 9/1999 |
| WO | WO-0041620 A1 | 7/2000 |
| WO | WO-0147597 A2 | 7/2001 |
| WO | WO-0157619 A2 | 8/2001 |
| WO | WO-02080762 A1 | 10/2002 |
| WO | WO-03075118 A2 | 9/2003 |
| WO | WO-03094720 A1 | 11/2003 |
| WO | WO-2004037080 A1 | 5/2004 |
| WO | WO-2006001005 A2 | 1/2006 |
| WO | WO-2006021956 A2 | 3/2006 |
| WO | WO-2007014545 A2 | 2/2007 |
| WO | WO-2007088315 A1 | 8/2007 |
| WO | WO-2008005015 A1 | 1/2008 |
| WO | WO-2008066682 A2 | 6/2008 |
| WO | WO-2010025166 A1 | 3/2010 |
| WO | WO-2010099066 A2 | 9/2010 |
| WO | WO-2010108287 A1 | 9/2010 |
| WO | WO-2010113354 A1 | 10/2010 |
| WO | WO-2010144626 A1 | 12/2010 |
| WO | WO-2011006356 A1 | 1/2011 |
| WO | WO-2011008838 A1 | 1/2011 |
| WO | WO-2011014292 A1 | 2/2011 |
| WO | WO-2011022942 A1 | 3/2011 |
| WO | WO-2011040877 A1 | 4/2011 |
| WO | WO-2011040878 A1 | 4/2011 |
| WO | WO-2011113070 A1 | 9/2011 |
| WO | WO-2011137375 A2 | 11/2011 |
| WO | WO-2011156374 A2 | 12/2011 |
| WO | WO-2012046158 A1 | 4/2012 |
| WO | WO-2012108895 A1 | 8/2012 |
| WO | WO-2012129413 A1 | 9/2012 |
| WO | WO-2012160550 A1 | 11/2012 |
| WO | WO-2013028960 A1 | 2/2013 |
| WO | WO-2013036307 A1 | 3/2013 |
| WO | WO-2013066642 A1 | 5/2013 |
| WO | WO-2013093690 A1 | 6/2013 |
| WO | WO-2013122788 A1 | 8/2013 |
| WO | WO-2013138500 A1 | 9/2013 |
| WO | WO-2013155196 A2 | 10/2013 |
| WO | WO-2013192166 A1 | 12/2013 |
| WO | WO-2014172451 A1 | 10/2014 |

OTHER PUBLICATIONS

Australian Design Awards. Heatplus Micro; printed from website http://www.designawards.com/au; printed on Apr. 12, 2002, 6 pages.
Bajaj, M.D.; "Event Recording in Ambulatory Patients with Syncopal Events"; University of Kansas; Wichita, Kansas; (no date); pp. 15-18; printed on or before Apr. 14, 2010.
Bluetooth. Headset Profile (HSP), printed from website http://bluetooth.com/English/Technology/Works/Pates/HSP.asgx, printed on May 12, 2010, 1 Page.
Bramanti et al., Multichannel telemetric system for biomedical signals via switched telephone lines, Medical and Biological Engineering and Computing, Sep. 1982, vol. 20, No. 5, pp. 653-656.
Burke, "A Micropower Dry-Electrode ECG Preamplifier", IEEE Transactions on Biomedical Engineering, Feb. 2000, vol. 47, No. 2, pp. 155-162.
Card Guard CG-6108 ACT Ambulatory Cardiac Telemetry Brochure; Card Guard; The Telemedicine Company: Switzerland; 2006, 2 pages.
Cardiocomm Solutions; Gems Air. (PC based on ECG management) printed from website http://www.cardiocommsolutions/com; printed on Mar. 19, 2010; 1 page.
Charuvastra. Transtelephonic Cardiac Event Recording for Arrhythmia Surveillance; printed from website http://tchin.org/resource room/c art• printed on Mar. 26, 2010• 2 pages.
Cheng, Allen C.; "Real-Time Cardiovascular Diseases Detection on a Smartphone"; Departments of Electrical And Computer Engineering, Bioengineering, Neurological Surgery and Computer Science; University of Pittsburgh; Pittsburgh, PA; printed on or before Apr. 14, 2010, 2 pages.
Chinese Patent Application No. 2013800135500 First Office Action dated Oct. 20, 2015.
Creative. PC-80B Portable ECG Monitor w/sd card extension slow; printed from website www.amazon.com/Portable-Monitor-extension-leather-shipping/dp/B0010jWKUE; printed on Feb. 4, 2010• 5 pages.
Deveau, "Health Care eyes smart phones to heal ills", printed from the website http://www.theQiobeandmail.com on Sep. 17, 2009, 4 pages.
Dinh. Heart activity monitoring on smartphone. IPCBEE—Int conf Biomedical Eng and Technol. Jun. 17-19, 2011. 11:45-49.
Dobrev, et al., Bootstrapped two-electrode biosignal amplifier, Med Bioi Eng Comput, 2008, 7 pages.
Dolan; Qualcomm launches ECG smartphone program in China; Sep. 8, 2011; 11 pgs.; retrieved Mar. 19, 2014 from the internet (http://mobihealthnews.com/13092/qualcomm-launches-ecg-smartphone-program-in-china/).
Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http:l/hypertextbook.com/facts/2003/ChrisDAmbrose.shtml).
European search report and opinion dated Nov. 21, 2014 for EP Application No. 11865699.0.
Favorite Plus. Handheld Easy ECG Monitor—Handheld EKG Monitor; printed from website www.favoriteplus.com/easy-ecg-handgeld-monitor-fp; printed on Feb. 4, 2010; 2 pages.
Favorite Plus. Handheld ECG Monitor—Handheld EKG Monitor at Favoriteplus.com; printed from website www.favoriteplus.com/handheld-ecg-ekg-monitor; printed on Feb. 4, 2010; 3 pages.
Favorite Plus. Handheld ECG Monitor—Handheld EKG Monitor InstantCheck; printed from website http://www. favoriteplus.com/instanchcheck-hand held-ecg-ekg-monitor; printed on Feb. 4, 2010; 2 pages.
Ferrick, M.D.; "Holter Monitoring and cardiac Event Recording in Assessing Symptomatic Patients"; Albert Einstein College of Medicine; Bronx, New York; (no date)• pp. 11-14• printed on or before Apr. 14, 2010.
Free2move. Vitaphone 2300; www.free2move.us/News/NewsVitaghone 240105.htm, printed May 12, 2010.
Fulford-Jones, et al., "A Portable, Low-Power, Wireless Two-Lead EKG System", Division of Engineering and Applied Sciences, Harvard University, Sep. 2004, 4 pages.
Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No IA02-1; May 11, 2012.
GBI Portal. Qualcomm's wireless reach mHealth project to improve cardiovascular disease in resource scarce China; Feb. 17, 2012; 7 pgs. Retrieved Mar. 19, 2014 from www.intergrallc.com/2012/02/17/qualcooms-wireless-reach-mhealth-project-to-improve-cardiovascular-disease-in-resource-scarce-china/.
GE; Healthcare., "Marquette heart rate turbulence analysis program", 2005, DC-1060-12.05-EN-US. 4 pages.
Gillette, M.D.; "Diagnosis of Pediatric Arrhythmias with Event Recording"; Medical University of South Carolina; Charleston, South Carolina; (no date); pp. 25-32; printed on or before Apr. 14, 2010.
Grier, James W.; "How to use 1-lead ECG recorders to obtain 12-lead resting ECGs and exercise ("stress") ECGs"; Department of Biological Sciences: printed from website http://www.ndsu.edu/pubweb/rvgrier; printed on Jun. 7, 2010; 13 pages.
Hannaford, Kat; "How To Turn Your iPhone Into A Laser, Fan or Flashlight"; printed from website htto://m.qizmodo.com/5534904•printed on Feb. 3, 2011, 2 pages.

(56) References Cited

OTHER PUBLICATIONS

Hartmann, "ECG Front-End Design is Simplified with MicroConverter" AnalogDialogue, Nov. 2003, vol. 37, pp. 1-5.
Hayes, M.D.; "Approaches to Diagnosing Transient Arhthmias" An Overview; Mayo Clinic; Rochester Minnesota; (no date); pp. 7-10; printed on or before Apr. 14, 2010.
Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.orglhlasurvival1.html).
Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/0ctober2007/Ciinca1Huang0ctober2007.aspx).
IMEC News; IMEC extends flexible ECG patch to enable arrhythmia detection; printed from website http://www2.imec.be/imeC' printed on Aug. 18, 2009 1 page.
Instromedix. Cardiac Event Recording FAQ's; Instromedix A Card Guard Company, San Diego, CA.; printed from website www.instromedix.com/pdf/products/cardiac; printed on or before Apr. 14. 2010.
Instromedix. The Arrhythmia Monitoring System; King of Hearts Express AF Recorder Brochure from Instromedix• A CardGuard Company; Rosemont IL; 2004• 3 pages.
International preliminary report on patentability dated Jul. 29, 2014 for PCT/US2013/023370.
International search report and written opinion dated Feb. 12, 2015 for PCT Application No. US2014/054414.
International search report and written opinion dated Feb. 17, 2012 for PCT/US2011/039445.
International search report and written opinion dated Apr. 27, 2012 for PCT/US2011/053708.
International search report and written opinion dated Apr. 30, 2015 for PCT/US2014/070170.
International search report and written opinion dated May 15, 2013 for PCT/US2013/023370.
International search report and written opinion dated Dec. 17, 2013 for PCT/2013/055458.
International search report dated Sep. 1, 2014 for PCT/US2014/034350.
International search report dated Dec. 10, 2013 for PCT/US2013/057576.
Jenkins II, W.; Time/Frequency Relationships for an FFT-Based Acoustic Modem; Naval Postgraduate School: pp. 1-102; Sep. 2010 (http://edocs.nps.edu/npspubs/scholarly/theses/2010/Sep/1 OSep_Jenkins.pdf) printed Feb. 10, 2013.
Kim, et al., "Detection of Atrial Fibrillation Episodes using Multiple Heart Rate Variability Features in Different Time Periods." Conference Proceedings IEEE Eng Med Biol Soc EMBS, 30th Annual International Conference, Aug. 20-25, 2008 pp. 5482-5485.
Koerner. The Author's Metrics; Wired Magazine Article; New York, NY; Jul. 2009; pp. 93-126.
Kumar, M.D., "Zio Patch"; printed from website http://www.irhythmtech.com/zio-solution/zio-gach/, grinted on Apr. 12, 2010.
Kumparak, Greg; "Visa officially announces their case that turns your iPhone into a credit card (and we've got pies!)"; May 17, 2010; printed from website www.mobilecrunch.com•printed on Feb. 3, 2011.
Lau, et al. iPhone ECG application for community screening to detect silent atrial fibrillation: A novel technology to prevent stroke. Int J Cardiol. Apr 30;165(1):193-4.
Lau, et al. Performance of an Automated iPhone ECG Algorithm to Diagnose Atrial Fibrillation in a Community AF Screening Program (Search-AF). Heart, Lung and Circulation. 2013; 22:S205.
Lau et al. Validation of an iPhone ECG application suitable for community screening for silent atrial fibrillation—A novel way to prevent stroke (Presentation Abstract 16810); American Heart Association 2012 Scientific Sessions and Resuscitation Science Symposium; 126(1); Nov. 20, 2012, 2 pages.
Leijdekkers et al., "Trial Results of a Novel Cardiac Rhythm Management System using Smart Phones and wireless ECG Sensors", Proceedings ofthe International Conf. On Smart homes and health Telematics., Jul. 1-3, 2009, Tours, France, 8 pages.
Levkov et al., "Removal of power-line interference from the ECG: a review of the subtraction procedure" BioMedical Engineering Online 2005, printed from website http://www.biomedical-engineeringonline.com/contenU4/1/50 pp. 1-18.
Lin; et al., "An intelligent telecardiology system using a wearable and wireless ECG to detect atrial fibrillation.", May 2010, 14(3), 726-33.
Lowres, et al. Screening Education And Recognition in Community pHarmacies of Atrial Fibrillation to prevent stroke in an ambulant population aged =65 years (Search-AF stroke prevention study): a cross-sectional study protocol. BMJ Open. Jun. 25, 2012; 2(3)e001355.
M Med Choice. Handheled ECG Monitor Brouchure; M Med Choice, Beijing Choice Electronic Technology Co. LTD.• published on or before Apr. 14, 2010, 6 pages.
M Med Choice. Handheld ECG Monitor MD100A1; printed from website http://www.choicemmed.com/products.as_p; printed on 12/28/2009; 2 pages.
M Med Choice. Handheld ECG Monitor MD100B; printed from website http://www.choicemmed.com/productshow.asp; printed on Dec. 28, 2009• 2 pages.
M Med Choice, printed from website http://www.choicemmed.con/1xwm .asp; printed on Dec. 28, 2009• 1 page.
MacFarlane, et al. Resting 12-lead ECG electrode placement and associated problems; SCST update 1995; 15pgs. Printed Feb. 18, 2014 from www.scst.org.uk/resources/RESTING_12.pdf.
Mauvila ECG Tutorial; Basic ECG Interpretation Tutorial; Sections 1-12; printed website http://mauvila.com/ECG/ecg.htm• printed on Mar. 26, 2010• 56 pages.
Medgadget. Zio Patch Wins Medical Design Award.MedGadget internet journal of emerging medical technologies, 2010, 1 page, printed from website: http://medaadaet.com/archives/2010/04/zio_patch_wins_medial_design_award_1.html.
MiCardioMobile: Remote Wireless Cardiac Rehabilitation Monitoring printed from website htto://alivetec.cable.nu/cardiomobile• printed on or before Apr. 14, 2010, 1 page.
Mobility Mind. Use your Treo 650 as a portable ECG monitoring device, Mobility Mind Celebrating mobile Internet lifestyle and culture, Sep. 14, 2005, 1 page. printed from website httg://treotoday.net/2005/09/14/use-your-treo-650-as-a-portab le-ecg-monitoring-device/.
Modem Protocols Explained; ftp://kermit.columbia.edu/kermit/cu/protocol.html; 5 pgs.; printed Oct. 2, 2013.
Modem Tutorial; http://www.lsu.edu/OCS/its/unix/tutoriai/ModemTutoriai/ModemTutorial.html; 2 pgs.; printed Oct. 2, 2013.
Muench, Frederick, PhD; "HRV; The Manurfacturers and Vendors Speak; The portable StressEraser Heart Rate Variability Biofeedback Device: Background and Research"• Biofeedback vol. 36 Issue 1, pp. 35-39• published Spring 2008.
Murph. RedEye mini converts iPhone, iPad or iPod into IR-beaming universal remote; printed from website http://www.engadget.com/2010/03/02/redeye; printed on Mar. 2, 2010; 3 pages.
Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).
Neuroreille; Audiometry; web version as of Oct. 14, 2008; 1 pg.; printed Jun. 6, 2012 (http://www.neuroreille.com/promenade/english/audiometry/audiometry.htm).
New Professional Quality ECGEKG Portable Heart Monitor; printed from website http://cgibay.com/ws/eBayiSAPl.dll• printed on Feb. 4, 2010• 3 pages.
Notice of allowance dated Aug. 28, 2012 for U.S. Appl. No. 13/420,520.
Notice of allowance dated Jul. 9, 2013 for U.S. Appl. No. 12/796,188.
Notice of allowance dated Dec. 4, 2013 for U.S. Appl. No. 14/015,303.
Notice of allowance dated Jan. 8, 2014 for U.S. Appl. No. 14/015,303.

(56) References Cited

OTHER PUBLICATIONS

Notice of allowance dated Jan. 27, 2014 for U.S. Appl. No. 14/015,303.
Notice of allowance dated Feb. 26, 2014 for U.S. Appl. No. 14/015,303.
Notice of allowance dated May 23, 2014 for U.S. Appl. No. 13/108,738.
Notice of allowance dated Mar. 29, 2016 for U.S. Appl. No. 14/254,310.
Notice of allowance dated Jun. 16, 2016 for U.S. Appl. No. 14/569,513.
Office action dated Jun. 18, 2012 for U.S. Appl. No. 13/420,520.
Office action dated Oct. 29, 2012 for U.S. Appl. No. 12/796,188.
Office action dated Jan. 2, 2014 for U.S. Appl. No. 13/108,738.
Office action dated Sep. 12, 2014 for U.S. Appl. No. 13/108,738.
Office action dated Oct. 6, 2014 for U.S. Appl. No. 14/252,044.
Office action dated Nov. 19, 2014 for U.S. Appl. No. 13/969,446.
Office Action dated May 18, 2015 for U.S. Appl. No. 13/752,048.
Office Action dated Aug. 25, 2015 for U.S. Appl. No. 14/479,105.
Office Action dated Oct. 6, 2015 for U.S. Appl. No. 14/589,513.
Office Action dated Dec. 21, 2015 for U.S. Appl. No. 13/964,490.
Office Action dated for Feb. 24, 2016 for U.S. Appl. No. 14/730,122.
Office Action dated Jun. 13, 2016 for U.S. Appl. No. 14/730,122.
Omron Portable ECG EKG Handheld HCG-801 Monitor; printed from website http://www.amazon.com/Omron-Portable-Handheld-HCG-801-Monitor/dp/B0019WH3EO• printed on Feb. 24, 2010• 5 pages.
Omron Portable ECG Monitor; printed from website http://www.target.com/gp/detail.html; printed on Mar. 26, 2010• 1 page.
Oresko, et al., "Detecting Cardiovascular Diseases via Real-Time Electrocardiogram Processing on a Smartphone", 2009 Workshop on Biomedicine in Computing: Systems, Architectures, and Circuits, pp. 13-16.
PCT Patent Application No. PCT/US2014/070170 International Preliminary Report on Patentability dated Jun. 23, 2016.
PCT/US2014/054414 International Preliminary Report on Patentability dated Mar. 16, 2016.
Perez, Sarah; No NFC? No Problem; New Startup Zoosh Provides Workaround Technology (Jun. 20, 2011); printed on or before Jun. 27, 2011 from website; 2 pgs.; (http://www.readwriteweb.com/archives).
Prystowsky, M.D.; "Chairmans Introduction"; Duke University Medical Center; Indianapolis, Indiana• (no date)• pp. 5-6• printed on before Apr. 14, 2010.
Prystowsky, M.D.; "Chairmans Summary"; Duke University Medical Center; Indianapolis Indiana; (no date); pp. 39-40• printed on or before Apr. 14, 2010.
Prystowsky, M.D., "The Clinical Application, Diagnostic Yield and Cost Considerations of Cardiac Event Recorders;", Indianapolis, Indiana (no date) pp. 19-23. printed on or before Apr. 14, 2010.
Puurtinen, et al., Best Electrode Locations for a Small Bipolar ECG Device; Signal Strength Analysis of Clinical Data, Annals of Biomedical Engineering, vol. 37, No.s 2, Feb. 2009 (© 2008) pp. 331-336.
Raju, Heart-Rate and EKG Monitor Using the MSP430FG439, SLAA280—Oct. 2005—Revised Sep. 2007, 11 pages.
Read-My-Heart. ECG Machine Handheld Read MyHeart; (product item No. HH-3413) printed from website http://www.helioliving.com/ECG-Machi ne-Handheld-ReadMyHea rt; printed on Feb. 4, 2010; 1 page.
Readmyheart Personal Handheld ECG Monitor with Free Illustrator Book & Free Electrodes V2.2; printed from website http://www.amazon.com/Readmyheart-Personai-Handheld-illustrator-Eiectrodes/dp/B0010AN63W; printed on Mar. 26, 2010; 4 pages.
Ricker. Square payment dongle demoed for iPhone toting hippies you (video); printed from website http://www.engadget.com/2010/01/18/square-payment; printed on Jan. 18, 2010; 6 pages.
Rockwood. The Networked Body Magazine Article from Fast Talk Magazine; Jul./Aug. 2009; pp. 19-26.

Salahhuddin, et al., "Ultra Short Term Analysis of Heart Rate Variability using Normal Sinus Rhythm and Atrial Fibrillation ECG Data", Engineering in Medicine and Biology Society, Aug. 2007, pp. 4656-4659.
Saxon, et al. iPhone rhythm strip—the implications of wireless and ubiquitous heart rate monitoring. JACC; 59(13):E726; Mar. 2012.
Saxon. Ubiquitous Wireless ECG Recording: A Powerful Tool Physicians Should Embrace. J Cardiobasc Elecrophysiol. 24(4):pp. 480-483; Apr. 2013.
Semler, M.D.; "The Future of Cardiac Event Monitoring"; St. Vincent Hospital and Medical Center; Portland Oregon; (no date); pp. 33-37; printed on or before Apr. 14, 2010.
SFO Medical. Choice Portable Handheld ECG EKG Monitor; printed from website http://www.amazon.com/Choice-Portable-Handheld-ECG-Monitor/dp/B001Q74VOM; printed on Mar. 26, 2010; 1 page.
Shenzhen New Element Med. Equipment. Wireless ECG Monitoring System, printed from website http://www.alibaba.com/product-gs/248168581/Wireless_ECG_Monitoring_system.html., printed on Mar. 26, 2010, 2 pages.
Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.
Smith. Smartphone may keep the cardiologist away, The Independent, Health & Families, Mar. 5, 2010, printed from website http://www.independent.co.uk/life-style/health-and-families/healthnews/smartghone-may-keep-the-cardiologist-away-1916652. html, printed on Mar. 26, 2010.
Stevens, "Apple's Seamlessly Embedded Heart Rate Monitor could turn the iPhone into a new-age mood ring", printed from the website http://www.enaadaet.com on May 6, 2010, 3 pages.
Talbeb Medical. Observer Hand-held ECG Monitor MD100B; (no date); printed on or before Apr. 14, 2010, 1 page.
Tei, et al., New index of combined systolic and diastolic myocardial performance: a simple and reproducible measure of cardiac function—a study in normals and dilated cardiomyopathy: J Cardiol.; 26(6):357-366; Dec. 1995.
Texas Instruments. Information for Medical Applications, "Biophysical Monitoring—Electrocardiogram (ECG) Front End", Apr. 2004, 2 pages.
Tschida. Power A's New Case Turns Your iPhone Into A Universal Remote; printed from website http://appadvice.com/appnn; printed on Mar. 1, 2010• 2 pages.
Vanhemert, Kyle; "XWave Headset Lets You Control iPhone Apps With Your Brain"; Sep. 8, 2010; printed from website http://gizmodo.com; printed on Sep. 8, 2010, 4 pages.
Vitaphone. Telemedicine since 1999: Modern health management is our special subject. 3 pgs. Retrieved Mar. 19, 2014 from www.vitaphone.de/en/company/history-of-vitaphone/.
Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).
Wikipedia; Aliasing; web version as of Apr. 3, 2011; 5 pgs.; printed Jun. 6, 2012 (http://liveweb.archive.org/http://en.wikipedia.org/w/index.php?title=Aiiasing&oldid=422141882).
Wikipedia: Hearing Range; web version as of Feb. 6, 2010; 5 pgs.; printed Jun. 6, 2012 (http://web.archive.org/web/201 002062137 41/http://en.wikipedia.org/wiki/Hearing_range).
Wikipedia. "Pulse oximetry", printed from website httg://en.wikigedia.org on May 10, 2010, 4 pages.
Wisneski, C.; Ultrasonic Local Area Communication; http://alumni.media.mit.edu/-wiz/ultracom.html; 2 pgs.; printed Oct. 2, 2013.
Woodward et al.; "Bio-Potential-To-Frequency Converter/Modulator"; Electronic Design• Aug. 1999, p. 177.
Ziegler, Chris; "EPI Life phone sports ECG function, can let doctors know if you're gonna make it "; printed from website www.enoadoet.com/2010/06/; Jun. 17, 2010, 3 pages.
U.S. Appl. No. 14/479,105 Office Action dated Jul. 22, 2016.
U.S. Appl. No. 14/494,191 Office Action dated Jul. 20, 2016.

\* cited by examiner

DISCORDANCE MONITORING

CROSS-REFERENCE

This application is a continuation of U.S. patent application Ser. No. 15/154,849, filed May 13, 2016, entitled "DISCORDANCE MONITORING", which claims the benefit of U.S. Provisional Application No. 62/161,092, filed May 13, 2015, both of which are incorporated herein by reference in its entirety.

BACKGROUND

Irregular heartbeats and arrhythmias are associated with significant morbidity and mortality in patients. Arrhythmias may occur continuously or may occur intermittently. Types of arrhythmia include atrial fibrillation and supraventricular tachycardia. Non-invasive cardiac monitoring is useful in diagnosing cardiac arrhythmia.

SUMMARY

Described herein are systems, devices, and methods for cardiac monitoring. The systems, devices, and methods described herein for cardiac monitoring may comprise portable computing devices such as smartphones, smartwatches, laptops, and tablet computers. Cardiac monitoring using the systems, devices, and methods described herein may be used to predict or identify the occurrence of arrhythmias.

Arrhythmias may occur continuously or may occur intermittently. Continuously occurring arrhythmias may be diagnosed using a number of different techniques including, for example, palpating a radial pulse of an individual, auscultating heart sounds of an individual, recording a heart rate of an individual, and recording an electrocardiogram of an individual. Because a continuous or essentially continuous arrhythmia is always present or essentially always present in the patient, any of the aforementioned diagnosis techniques may be applied at any time in order to make a diagnosis. For intermittent arrhythmia diagnosis any of the aforementioned diagnosis techniques may also be used, however, because intermittent arrhythmias do not always present, the diagnostic technique cannot be applied at any time, but must be applied at the time when the individual is experiencing the arrhythmia. Thus, diagnosing, intermittent arrhythmias may be difficult, because, for example, it is not practical to be prepared to apply one of the aforementioned diagnostic modalities at the exact time that an individual experiences an intermittent arrhythmia. This particular difficulty may also be compounded when an individual is not aware that they are experiencing an intermittent arrhythmia so that they would not, for example, seek out a health care provider during the intermittent arrhythmia.

However, certain parameter values may be conveniently sensed continuously such as, for example, heart rate and activity level, and analyzed to predict or determine the presence of an arrhythmia. One or more conveniently continuously sensed parameter values such as, for example, heart rate and activity level may be analyzed to determine the future onset of or the presence of an arrhythmia by identifying discordance between these two parameter values. For example, discordance between two sensed values may indicate the future onset of or the presence of an arrhythmia. In response to the identification of the future onset of or presence of an arrhythmia an electrocardiogram may be caused to be sensed.

Additional sensed parameters may also be used in an analysis as part of the cardiac monitoring systems, devices, and methods described herein. For example, a determined heart rate variability may be compared to a sensed heart rate and activity level to determine the presence of, for example, atrial fibrillation or supraventricular tachycardia.

Described herein is a method for cardiac monitoring, comprising: sensing an activity level value of an individual with a first sensor of a wearable device worn by said individual; sensing a heart rate value of said individual with a second sensor of said wearable device; determining a heart rate variability value with a processor of said wearable device; determining if a discordance is present between two or more of said activity level value, said heart rate value, and said heart rate variability value with said processor; and indicating to said individual with said wearable device to record an electrocardiogram when said discordance is determined to be present. In some embodiments, said first sensor comprises an accelerometer. In some embodiments, said first sensor comprises a gyroscope. In some embodiments, said second sensor comprises a photosensor. In some embodiments, said discordance is determined to be present when said activity level value is normal and said heart rate value is elevated. In some embodiments, said discordance is determined to be present when said activity level value is normal, said heart rate value is elevated, and said heart rate variability value is increased. In some embodiments, said method comprises indicating a presence of atrial fibrillation. In some embodiments, said discordance is determined to be present when said activity level value is normal, said heart rate value is elevated, and said heart rate variability value is decreased. In some embodiments, said method comprises indicating a presence of a supraventricular tachycardia. In some embodiments, setting one or more threshold values based on said activity level value, said heart rate value, and said heart rate variability value. In some embodiments, said one or more threshold values is determined using a machine learning algorithm.

Described herein is wearable device for cardiac monitoring, comprising: a processor; a first sensor configured to sense an activity level value of an individual, wherein said first sensor is coupled to said processor; a second sensor configured to sense a heart rate value of an individual, wherein said second sensor is coupled to said processor; a first electrode and a second electrode configured to sense an electrocardiogram; a non-transitory computer readable storage medium encoded with a computer program including instructions executable by said processor to cause said processor to: determine if a discordance is present between said activity level value of said individual and said heart rate value of said individual; and indicate that said electrocardiogram be recorded when said discordance is determined to be present. In some embodiments, said first sensor comprises an accelerometer. In some embodiments, said first sensor comprises a gyroscope. In some embodiments, said second sensor comprises a photosensor. In some embodiments, said discordance is determined to be present when said activity level value is normal and said heart rate value is elevated. In some embodiments, said computer program includes instructions that cause said processor to determine a heart rate variability value. In some embodiments, said discordance is determined to be present when said activity level value is normal, said heart rate value is elevated, and said heart rate variability value is increased. In some embodiments, said computer program includes instructions that cause said processor to indicate a presence of atrial fibrillation. In some embodiments, said discordance is determined to be present when said activity level value is normal, said heart rate value is elevated, and said heart rate variability value is elevated. In some embodiments, said computer program includes instructions that cause said processor to indicate a presence of a supraventricular tachycardia. In some embodiments, said computer program includes instructions that cause said processor to set one or more threshold values based on said activity level value, and said heart rate value.

In some embodiments, said one or more threshold values is determined using a machine learning algorithm.

Described herein is a method for cardiac monitoring, comprising: sensing an activity level value of an individual with a first sensor of a wearable device worn by said individual; sensing a heart rate value of said individual with a second sensor of said wearable device; determining if a discordance is present between two or more of said activity level value and said heart rate value by using an activity level threshold and a heart rate threshold with a processor of said wearable device; and adjusting said activity level threshold and said heart rate level threshold using a machine learning algorithm executed by said processor.

BRIEF DESCRIPTION OF THE DRAWINGS

The novel features of the individual matter described herein are set forth with particularity in the appended claims. A better understanding of the features and advantages of the present individual matter described herein will be obtained by reference to the following detailed description that sets forth illustrative embodiments, in which the principles of the individual matter described herein are utilized, and the accompanying drawings of which:

DETAILED DESCRIPTION

Cardiac Monitoring

Described herein are systems, devices, and methods for use in cardiac monitoring. Cardiac monitoring typically comprises monitoring of the heart function of an individual for changes in, for example, heart rate or heart rhythm.

Heart rate may vary between, for example, bradycardia which typically is defined as a heart rate of less than 60 beats per minute, normal resting heart rate which typically is defined as a heart rate of between 60-100 beats per minute, and tachycardia which typically is defined as a heart rate of greater than 100 beats per minute. Variance of heart rate over a period of time may be referred to as Heart Rate Variability (HRV).

Heart function is also measured in terms of regularity of rhythm. A normal heart rhythm comprises of a systole (ejection phase) and diastole (filling phase). During the phases of systole and diastole, the ventricles of the heart act in concert in a regular manner that is repeated with every single heartbeat. When there is an abnormality of rhythm, the condition is typically referred to as an arrhythmia. Examples of arrhythmias include atrial fibrillation, WPW syndrome, prolonged QT syndrome, and premature ventricular contractions.

Many arrhythmias occur intermittently and relatively infrequently. Thus, in order to monitor and capture an intermittent arrhythmia, continuous monitoring is typically required. ECGs can be measured continuously in the ambulatory patient using holter monitoring, but this type of monitoring is cumbersome for the patient and is thus not widely used. A device or system configured to take an intermittent ECG is much more convenient for users. Such devices or systems comprise a mobile computing device that includes one or more electrodes that sense an ECG when contacted by a skin surface of the patient. Such devices are light and portable and don't necessarily require the user to be in continuous physical contact with one or more electrodes as they would with a holter type monitor. Intermittent arrhythmias can be recorded with these devices and systems when a user is given an indication that an intermittent arrhythmia is occurring. HRV sensing is used in combination with these devices or systems to indicate to a user when to contact one or more electrodes in order to sense an ECG.

Figure 1:
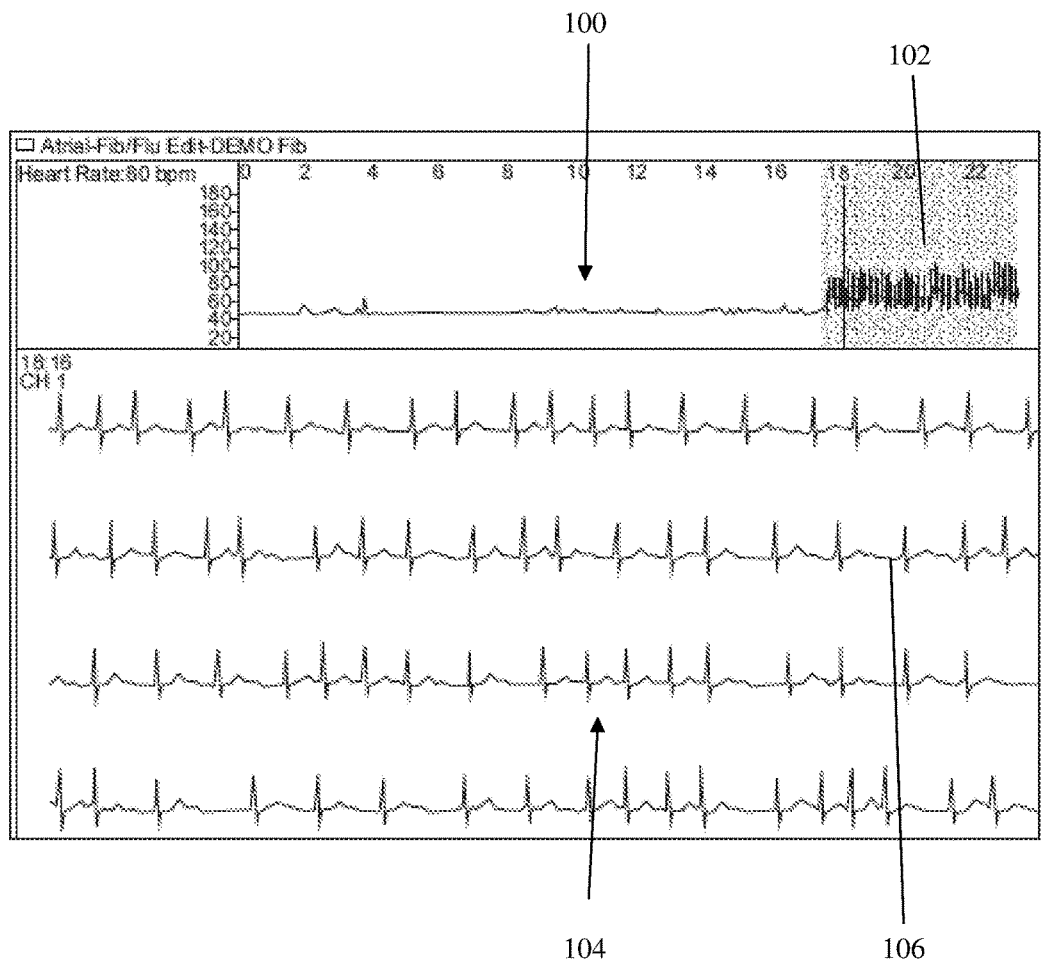
FIG. 1 shows a heart rate tracing with a corresponding electrocardiogram (ECG) tracing both sensed from the same individual over the same period.

FIG. 1 shows a heart rate tracing 100 with a corresponding electrocardiogram (ECG) tracing 104 both sensed from the same individual over the same period. As is shown in the ECG tracing 104, the individual experienced a period of intermittent atrial fibrillation 106 during the time that the ECG was sensed. As is also shown in the heart rate tracing 100, the heart rate of the individual rapidly increased 102 during the period of intermittent atrial fibrillation. As such, the HRV of the individual increased during the period of intermittent atrial fibrillation as the heart rate of the individual increased from a resting heart rate to an increased heart rate 102. HRV changes are therefore associated with atrial fibrillation, wherein increased HRV is found during periods of intermittent atrial fibrillation.

Figure 2:
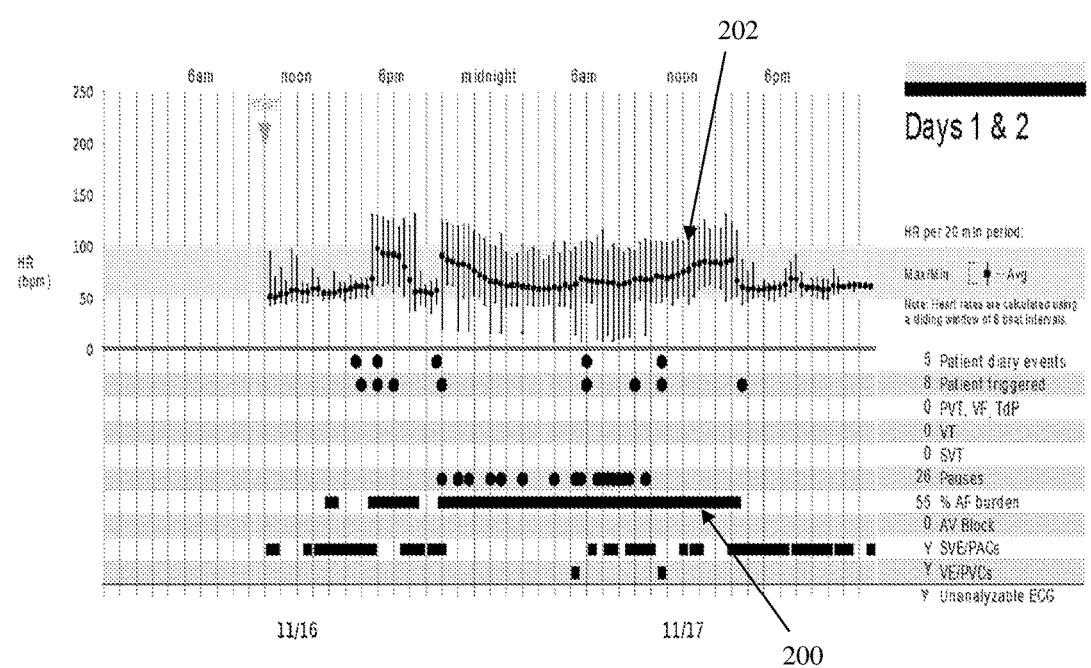
FIG. 2 shows a graphic showing both heart rate and rhythm analysis over a period of time in an individual who experienced different arrhythmias.

FIG. 2 shows a graphic showing both heart rate 202 and rhythm analysis 200 over a period of time in an individual who experienced different arrhythmias. As shown, the measured heart rate 202 tended to increase above 100 beats per minute during the periods of sensed atrial fibrillation 200. Thus, elevated heart rate above resting heart rate occurred in this individual during the period of arrhythmia.

Figure 3:
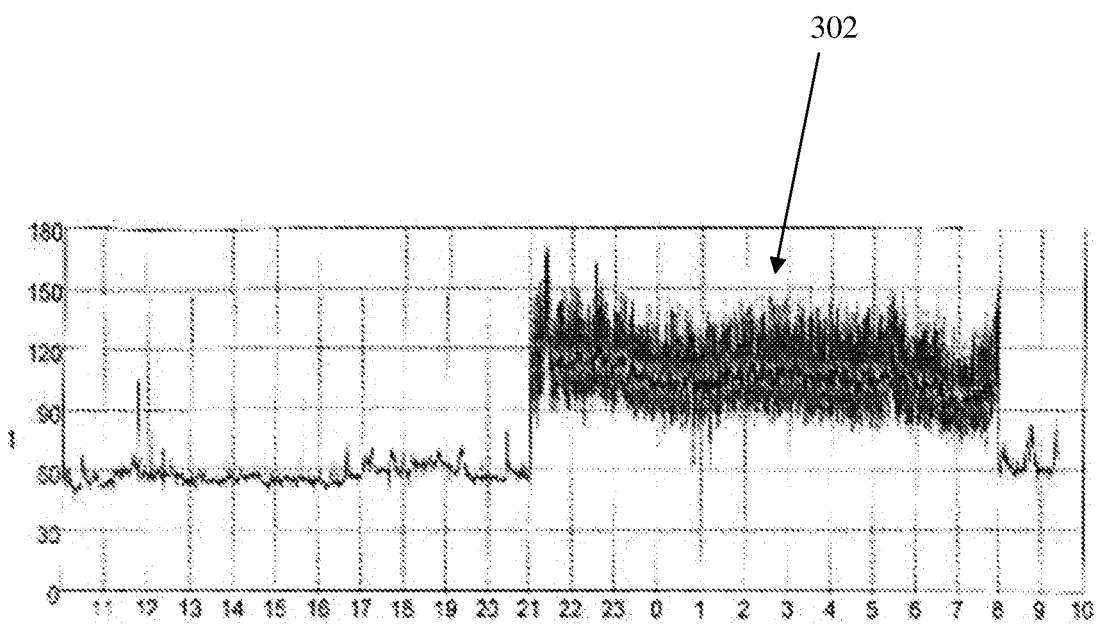
FIG. 3 shows a close up of a heart rate tracing sensed over a period of paroxysmal atrial fibrillation.

FIG. 3 shows a close up of a heart rate tracing sensed over a period of paroxysmal atrial fibrillation. As shown, there was a substantial step increase from a normal heart of between 60-100 beats per minute to above 100 beats per minute 302 during the period of atrial fibrillation.

Figure 4:
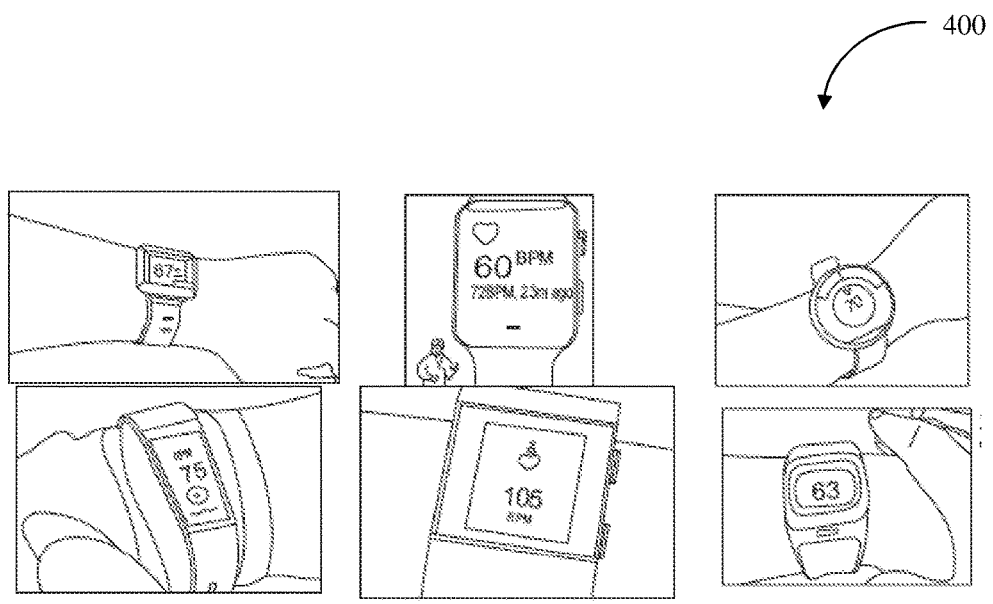
FIG. 4 shows available technologies for continuously sensing a heart rate or an activity level.

FIG. 4 shows available technologies 400 for continuously sensing a heart rate or an activity level. Shown are smartwatches made available by manufactures such as, for example, Apple. A wearer of one of the shown smartwatch technologies 400 may conveniently and continuously wear one or more sensors that are either coupled to or integrated with the watch throughout the day, thus, effectively continuously monitoring one or more parameter values via the one or more sensors that are either coupled to or integrated with the smartwatch. Thus, one of the smartwatch technologies 400 are an example of a type of device in the form of a wearable that conveniently provides continuous monitoring of one or more parameters of a user. Non-limiting examples of wearable devices that may have one or more sensors either coupled to them or integrated with them include watches (e.g. smartwatches), eyeglasses, wristbands, necklaces, and clothing. The one or more continuously sensed parameters of the user of such a technology as, for example, shown in FIG. 4, are then used to indicate to the user to use a device or system to sense an ECG. For example, a user wearing a smartwatch having a heart rate sensor is alerted by the smartwatch to record an ECG when the HRV of the user increases.

Figure 5:
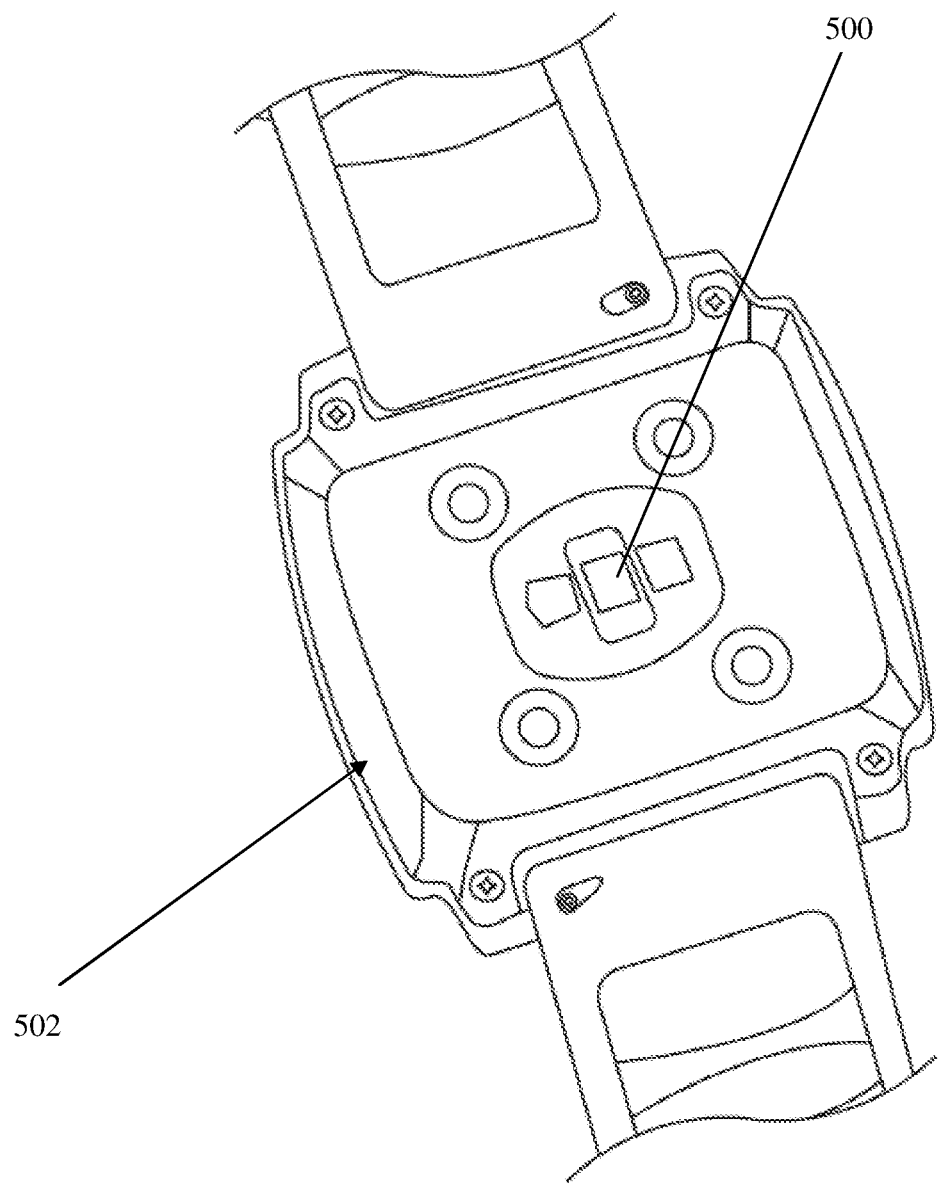
FIG. 5 shows a photosensor commonly used to measure heart rates integrated with a smartwatch.

FIG. 5 shows a photosensor 500 commonly used to measure heart rates integrated with a smartwatch 502.

Activity level is correlated with arrhythmia in many individuals who have a predisposition to develop arrhythmia wherein increased activity level is associated with onset of arrhythmia. In other individuals an increased activity level that is detected by one or more activity sensors in the presence of increased HRV is likely normal and is not associated with arrhythmia. Thus, as described herein, the addition of continuous heart rate monitoring along with continuous activity level monitoring may achieve the same results, in terms of arrhythmia monitoring, as continuous electrocardiogram monitoring. Using one or more sensors associated with the devices or systems described herein two parameter values of heart rate and activity level may be conveniently and accurately continuously and simultaneously sensed.

Devices and Systems

Figure 6:
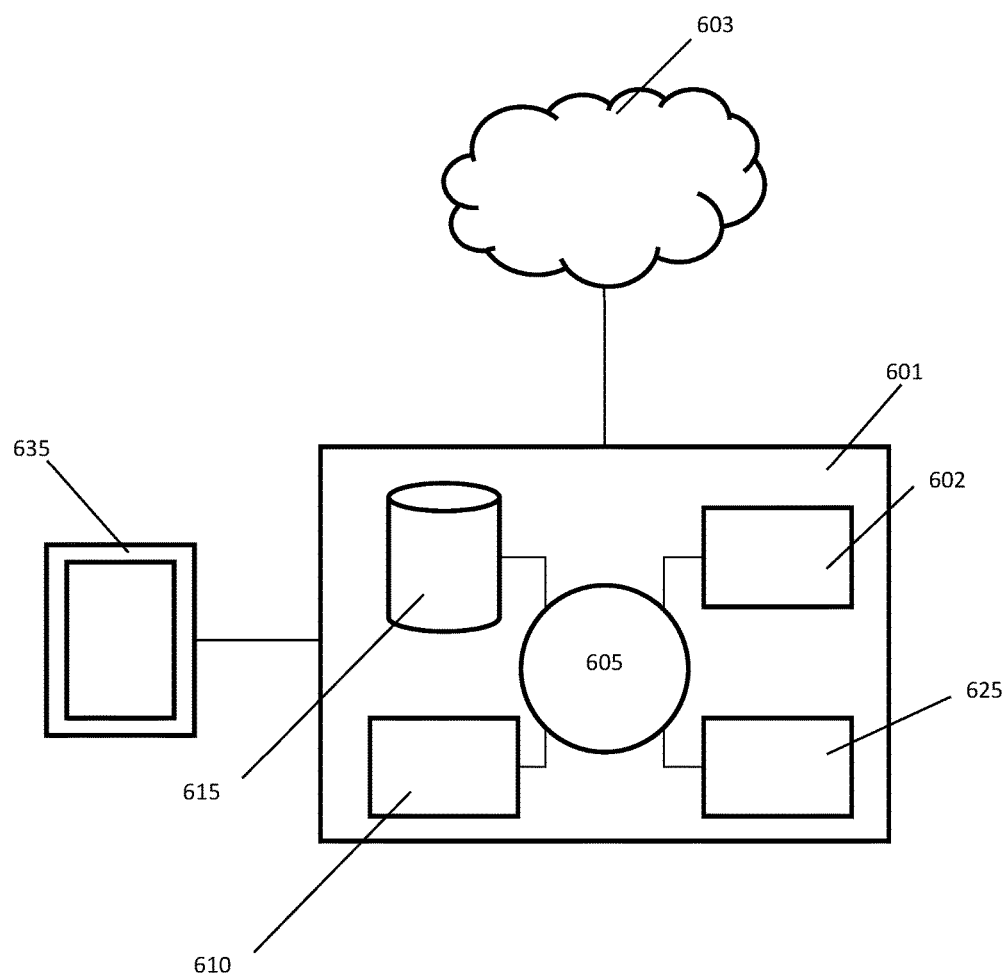
FIG. 6 exemplifies a computer system that is programmed or otherwise configured to sense one or more physiologic parameters of an individual.

FIG. 6 exemplifies a computer system 601 that is programmed or otherwise configured to sense one or more physiologic parameters of an individual. Non-limiting examples of physiologic parameters include heart rate, blood pressure, temperature, oxygen saturation, ECG, HRV, and activity level. The computer system 601 comprises an electronic device of a user 635, or comprises a computer system that is remotely located with respect to the electronic device 635. Electronic devices suitable for use with the system 601 include mobile electronic devices such as smartphones, smartwatches, tablets, and laptops. The electronic device 601 comprises one or more sensors configured to sense a physiologic parameter. Numerous sensors are known for measuring heart rate. Non-limiting examples of suitable sensors include light based sensors such as, for example, infrared sensor/emitter, ultrasound sensors, and tactile sensors. Sensors for measuring rhythm include electrodes for measuring electrocardiograms (ECG) and light based sensors for measuring photoplethysmograms.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 602 (e.g., network adapter) for communicating with one or more other systems, and peripheral devices 625, such as cache, other memory, data storage and/or electronic display adapters. The memory 610, storage unit 615, interface 602 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 603 with the aid of the communication interface 602. The network 603 can be the Internet, an internet and/or extranet, or an intranet and/or extranet that is in communication with the Internet. The network 603 in some cases is a telecommunication and/or data network. The network 603 can include one or more computer servers, which can enable distributed computing, such as cloud computing. The network 603, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 603. For instance, the computer system 601 can communicate with a remote computer system of a user (e.g., mobile device, server, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 603.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory)

or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution The computer system 601 can include or be in communication with an electronic display 535 that comprises a user interface (UI) 640 for providing, for example, distributions of magnetic fields, distributions of electrical currents, distributions of local myocardial activities, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm, for example, is used to analyze a sensed physiologic parameter.

A device as described herein is in some embodiments configured to sense two or more physiologic parameters. For example, a device configured to measure the heart rate of an individual as described herein is also in some embodiments configured to sense the electrocardiogram of said individual. In these embodiments, a device as described herein includes one or more electrodes configured to sense an electrocardiogram of an individual. In some embodiments, a device as described herein comprises two electrodes. In some embodiments, a device as described herein comprises three electrodes. In some embodiments, a device as described herein comprises four electrodes. In some embodiments, a device as described herein comprises five electrodes. In some embodiments, a device as described herein comprises six electrodes. In some embodiments, a device as described herein comprises seven electrodes. In some embodiments, a device as described herein comprises eight electrodes. In some embodiments, a device as described herein comprises nine electrodes. In some embodiments, a device as described herein comprises ten electrodes. Electrodes of the device described herein are configured to sense an electrocardiogram of an individual and transmit the sensed electrocardiogram data to a processor integrated with the device or part of the system described herein. In some embodiments, the processor is configured to display the electrocardiogram on a display of the device described herein. In some embodiments, the device is configured to sense and/or display a single lead electrocardiogram. In some embodiments, the single lead comprises any of Lead I, Lead II, Lead aVR, Lead aVL, Lead aVF, Lead V1, Lead V2, Lead V3, Lead V4, Lead V5, and Lead V6. In some embodiments, the device is configured to sense and/or display two leads comprising any two of Lead I, Lead II, Lead aVR, Lead aVL, Lead aVF, Lead V1, Lead V2, Lead V3, Lead V4, Lead V5, and Lead V6. In some embodiments, the device is configured to sense and/or display two leads comprising any three of Lead I, Lead II, Lead aVR, Lead aVL, Lead aVF, Lead V1, Lead V2, Lead V3, Lead V4, Lead V5, and Lead V6. In some embodiments, the device is configured to sense and/or display three leads comprising any three of Lead I, Lead II, Lead aVR, Lead aVL, Lead aVF, Lead V1, Lead V2, Lead V3, Lead V4, Lead V5, and Lead V6. In some embodiments, the device is configured to sense and/or display four leads comprising any four of Lead I, Lead II, Lead aVR, Lead aVL, Lead aVF, Lead V1, Lead V2, Lead V3, Lead V4, Lead V5, and Lead V6. In some embodiments, the device is configured to sense and/or display five leads comprising any five of Lead I, Lead II, Lead aVR, Lead aVL, Lead aVF, Lead V1, Lead V2, Lead V3, Lead V4, Lead V5, and Lead V6. In some embodiments, the device or system is configured to sense and/or display six leads comprising any six of Lead I, Lead II, Lead aVR, Lead aVL, Lead aVF, Lead V1, Lead V2, Lead V3, Lead V4, Lead V5, and Lead V6. In some embodiments, the device is configured to sense and/or display seven leads comprising any seven of Lead I, Lead II, Lead aVR, Lead aVL, Lead aVF, Lead V1, Lead V2, Lead V3, Lead V4, Lead V5, and Lead V6. In some embodiments, the device is configured to sense and/or display eight leads comprising any eight of Lead I, Lead II, Lead aVR, Lead aVL, Lead aVF, Lead V1, Lead V2, Lead V3, Lead V4, Lead V5, and Lead V6. In some embodiments, the device is configured to sense and/or display nine leads comprising any nine of Lead I, Lead II, Lead aVR, Lead aVL, Lead aVF, Lead V1, Lead V2, Lead V3, Lead V4, Lead V5, and Lead V6. In some embodiments, the device is configured to sense and/or display ten leads comprising any ten of Lead I, Lead II, Lead aVR, Lead aVL, Lead aVF, Lead V1, Lead V2, Lead V3, Lead V4, Lead V5, and Lead V6. In some embodiments, the device is configured to sense and/or display eleven leads comprising any eleven of Lead I, Lead II, Lead aVR, Lead aVL, Lead aVF, Lead V1, Lead V2, Lead V3, Lead V4, Lead V5, and Lead V6. In some embodiments, the device is configured to sense and/or display twelve leads comprising any twelve of Lead I, Lead II, Lead aVR, Lead aVL, Lead aVF, Lead V1, Lead V2, Lead V3, Lead V4, Lead V5, and Lead V6. In some embodiments, the device includes software configured to cause a processor of said device to analyze the sensed electrocardiogram. An analysis of a sensed electrocardiogram performed by the processor of the device identifies the presence of an abnormal heart condition. For example, an analysis performed by a processor of a device, in some embodiments, identifies arrhythmias by, for example, analysis of the PQRST waveform and/or comparing multiple PQRST waveforms within an electrocardiogram. In some embodiments, the processor carries out an analysis of an electrocardiogram by comparing one or more PQRST waveforms of an individual against a one or more PQRST waveforms of other individuals from a database containing electrocardiograms of other individuals. In some embodiments of the devices described herein, an individual is alerted to sense an electrocardiogram by, for example, engaging one or more electrodes when the device senses one or more physiologic parameters. For example, in some embodiments, a device as described herein is configured to sense a blood pressure of an individual, and in some of these embodiments, the device is configured to sense a second physiologic parameter of the individual such as for example a heart rate. An accelerated heart rate of an individual sensed by the device in addition to, for example, a low blood pressure of the individual concurrently sensed by the device, triggers the processor of the device to indicate to the individual to engage with the electrodes of the device in order to sense an electrocardiogram.

The combination of a sensed accelerated heart rate and low blood pressure typically indicate an abnormality, however, other physiologic conditions may also produce an elevated heart rate accompanied by low blood pressure including, for example, dehydration. Thus, in some embodiments, accuracy is enhanced when physiologic parameters such as, for example, heart rate, blood pressure, oxygen saturation, and temperature are compared to baseline values of the individual or to a data from a database containing the physiological parameters of other individuals. Some elite athletes, for example, have physiologic parameter values that would be abnormal in another individual such as, for example, very low heart rates or increased heart rate variability (e.g. during a period of exercise).

A device as described herein is in some embodiments configured to sense a photophletysmogram of an individual. A photopletysmogram, for example, provides cardiac cycle information and may, for example, be analyzed by a processor of a device described herein to determine a presence of a premature ventricular contraction.

In some embodiments, a device as described herein is configured to sense a pulse oxygenation of an individual. A device as described herein is configured to sense a pulse oxygenation of an individual in some embodiments.

Analysis

In some embodiments, a device as described herein is configured to sense and/or analyze a number of additional physiologic parameters. Non-limiting examples of parameter values sensed and/or analyzed by the devices and systems described herein include heart rate, activity level, blood pressure, temperature, pulse oxygen, and heart rate variability. Analysis includes in some embodiments the comparison of a first sensed physiologic parameter to a second sensed physiologic and determining if a discordance exists between the first and second sensed parameter values.

In some embodiments, a device as described herein is configured to monitor for arrhythmia in an individual, wherein monitoring may comprise the identification of onset of an arrhythmia. In some embodiments, cardiac monitoring carried out by the devices described herein comprises, for example, monitoring for the presence or onset of arrhythmia in an individual who has not previously been identified to have an arrhythmia. In some embodiments, cardiac monitoring carried out by the devices described herein comprises the identification of onset of a known or suspected intermittent arrhythmia. In some embodiments, the devices described herein are configured to predict an onset of an arrhythmia in an individual. The onset of an arrhythmia is, for example, predicted due to a sudden and significant shift in the value of a sensed physiologic parameter such as heart rate. A prediction of arrhythmia is more accurate when two or more physiologic parameters are concurrently sensed and analyzed with respect to one another. For example, sensing of heart rate changes with respect to a sensed activity level provides contextual information for the sensed heart rate.

A subset of arrhythmias are sometimes termed tachyarrhythmias. Tachyarrhythmias typically comprise a tachycardic heart rate which may comprise a heart rate above 100 beats per minute. Tachyarrhythmias may comprise, for example, certain types of atrial fibrillation and supraventricular tachycardia. In some embodiments, the devices as described herein are configured to identify the presence or onset of a tachyarrhythmia, such as, for example, atrial fibrillation or supraventricular tachycardia. In some embodiments, the devices as described herein are configured to identify the presence or onset of a tachyarrhythmia. In some embodiments, the devices as described herein are configured to predict the onset of a tachyarrhythmia.

In some embodiments, the devices as described herein are configured to provide continuous cardiac monitoring. In some embodiments, the devices as described herein are configured to provide continuous cardiac monitoring for a period of up to one year. In some embodiments, the devices as described herein are configured to provide continuous cardiac monitoring for a period of up to 12 months. In some embodiments, the devices described herein are configured to provide continuous cardiac monitoring for a period of up to 6 months. In some embodiments, the devices described herein are configured to provide continuous cardiac monitoring for a period of up to 3 months. In some embodiments, the devices described herein are configured to provide continuous cardiac monitoring for a period of up to 1 month. In some embodiments, the devices described herein are configured to provide continuous cardiac monitoring for a period of up to 2 weeks. In some embodiments, the devices described herein are configured to provide continuous cardiac monitoring for a period of up to 1 weak. In some embodiments, the devices described herein are configured to provide continuous cardiac monitoring for a period of up to 72 hours. In some embodiments, the devices described herein are configured to provide continuous cardiac monitoring for a period of up to 48 hours. In some embodiments, the devices described herein are configured to provide continuous cardiac monitoring for a period of up to 24 hours. In some embodiments, the devices described herein are configured to provide continuous cardiac monitoring for a period of up to 12 hours. In some embodiments, the devices described herein are configured to provide continuous cardiac monitoring for a period of up to 8 hours. In some embodiments, the devices described herein are configured to provide continuous cardiac monitoring for a period of up to 4 hours. In some embodiments, the devices described herein are configured to provide continuous cardiac monitoring for a period of up to 2 months.

In some embodiments, the devices described herein are configured to provide intermittent cardiac monitoring. In some embodiments, intermittent cardiac monitoring is initiated in response to one or more sensed parameter values. Non-limiting examples of the one or more sensed parameter value that may cause initiation of intermittent cardiac monitoring may comprise, for example, a heart rate of an individual, a blood pressure of an individual, an activity level an individual, a temperature of an individual, a pulse oximetry of an individual, or any other sensed biometric parameter of an individual. In some embodiments, an electrocardiogram of an individual may be sensed in response to one or more sensed parameters. For example, an electrocardiogram may be caused to be sensed in response to a heart rate value.

In some embodiments, one or more continuous sensors may sense one or more parameters that cause the initiation of intermittent cardiac monitoring by one or more sensors. In some embodiments, a heart rate of an individual is sensed continuously. In some embodiments, an activity level of an individual is sensed continuously. In some embodiments, a heart rate variability of an individual is sensed continuously. In some embodiments, an electrocardiogram of an individual is sensed intermittently. In some embodiments, an intermittently sensed electrocardiogram is caused to be sensed in response to a continuously measured heart rate of an individual. In some embodiments, an intermittently sensed electrocardiogram is caused to be sensed in response to an activity level of an individual. In some embodiments, an intermittently sensed electrocardiogram is caused to be sensed in response to both a continuously measured heart rate and a continuously measured activity level. In some embodiments, an intermittently sensed electrocardiogram is caused to be sensed in response to a continuously sensed heart rate, a continuously sensed activity level, and a continuously sensed heart rate variability.

In some embodiments, a device or system as described herein comprises one or more sensors configured for continuous cardiac monitoring. In some embodiments, a device or system as described herein comprises one or more sensors configured for intermittent cardiac monitoring. In some embodiments, a device or system as described herein comprises one or more heart rate sensors, which may, for example, comprise a photosensor. In some embodiments, a device or system as described herein comprises one or more activity level sensors, which may, for example, comprise an accelerometer or a gyroscope. In some embodiments, a device or system as described herein comprises one or more electrocardiogram sensors, which may, for example, comprise one or more electrodes. Non-limiting examples of other sensors suitable for use with the devices, systems, and methods described herein further comprise blood pressure sensors, temperature sensors, and pulse oximetry sensors.

In some embodiments, a device or system as described herein comprises a processor. In some embodiments, a process is coupled with one or more sensors that are configured to sense continuously and one or more sensors that are configured to sense intermittently. In some embodiments, a processor is configured to receive parameter values from one or more sensors. In some embodiments, a processor is configured to activate one or more sensors or to initiate the sensing of a parameter value. In some embodiments, a processor is configured to analyze a parameter value. In some embodiments, a processor is configured to compare a first parameter value with a second parameter value. In some embodiments, a first and a second parameter value to be compared are simultaneously or essentially simultaneously sensed.

In some embodiments, a device or system as described herein further comprises software in the form of a program or application. In some embodiments, the program or application may be configured to cause a processor to carry out one or more functions. In some embodiments, the program or application may be configured to cause a processor to receive parameter values from one or more sensors. In some embodiments, the program or application may be configured to cause a processor to activate one or more sensors or to initiate the sensing of a parameter value. In some embodiments, the program or application may be configured to cause a processor to analyze a parameter value. In some embodiments, the program or application may be configured to cause a processor to compare a first parameter value with a second parameter value. In some embodiments, a first and a second parameter value to be compared are simultaneously or essentially simultaneously sensed.

In some embodiments, the devices described herein are configured to carry out an analysis, wherein the analysis is performed by a processor. In some embodiments, an analysis of one or more parameter values carried out by the devices described herein comprises a comparison of a sensed parameter value to a threshold or range. For example, an analysis may comprise determining whether a sensed heart rate value falls within one or more ranges. For example, in some embodiments, a sensed heart rate may be determined to be within a heart rate range comprising a range between 60-100 beats per minute. For example, in some embodiments, a sensed heart rate may be determined to be in a heart rate range comprising a range of values less than 60 beats per minute. For example, in some embodiments, a sensed heart rate may be determined to be within a heart rate range comprising a range of values above 100 beats for minute.

In some embodiments, an analysis of one or more parameter values carried out by the devices described herein comprises a comparison of a first sensed parameter to a second sensed parameter. For example, in some embodiments, a heart rate value is compared to a sensed activity level of an individual.

In some embodiments, a first sensed value is compared to a second sensed value, and it is determine whether a discordance exists between the two values. For example, in some embodiments, an elevated heart rate value would be expected to be present during a period of elevated activity, thus an elevated heart rate and an elevated activity level that are simultaneously sensed would not be found to be in discordance with one another.

A discordance may be identified when a first sensed parameter value would not be expected to coincide with a second sensed parameter value. For example, an elevated heart rate value would not be expected to be present with a normal or resting activity level and thus the two values are in discordance with one another. For example, in some embodiments, when a heart rate sensor senses a heart rate above 100 beats per minute and a simultaneously sensed activity level is determined to be a resting activity level, an analysis of the two sensed values determines that they are in discordance with one another.

In some embodiments, an analysis carried out by the devices and systems described herein comprises the determination of an increase in a heart rate variability. In some embodiments, an analysis carried out by the devices and systems described herein comprises comparing a heart rate variability with one or more sensed parameter values. For example, in some embodiments, a heart rate variability is compared to concurrently or essentially concurrently sensed heart rate and activity level values.

In some embodiments, an analysis carried out by the devices and systems described herein comprises the prediction of or the identification of the initiation of an arrhythmia using an identified discordance as described herein. In some embodiments, a discordance comprising a simultaneously or essentially simultaneously sensed elevated heart rate and resting or normal activity level is determined to indicate the imminent initiation of an arrhythmia or the presence of an arrhythmia. In particular, because the heart rate is elevated, the arrhythmia with this type of discordance typically comprises a tachyarrhythmia.

In some embodiments, a simultaneously sensed increase in heart rate variability, an elevated heart rate, and a resting or normal activity rate is determined to indicate the future onset or presence of atrial fibrillation. In some embodiments, a sensed increased heart rate variability, normal resting heart rate, and resting or normal activity rate may also be determined to indicate the future onset of or the presence of atrial fibrillation. In some embodiments, a simultaneously sensed decrease in heart rate variability, an elevated heart rate, and a resting or normal activity rate is determined to indicate the future onset or presence of supraventricular tachycardia. In some embodiments, when an arrhythmia is determined to be imminent or present, an electrocardiogram is recorded. In some embodiments, an individual is instructed or signaled by a cardiac monitoring device or system described herein to engage one or more electrodes in order to sense in electrocardiogram. In some embodiments, one or more electrodes may be positioned on a surface of a cardiac monitoring device so that the individual may, for example, comfortably engage a first electrode with a skin surface of a first extremity while simultaneously engaging a second electrode with a skin surface of a second extremity. In some embodiments, one or more electrodes may be affixed to an individual's body and are automatically engaged to sense an electrocardiogram by a cardiac monitoring device or system when an arrhythmia is determined to be imminent or present in the individual. For example, a first electrode may be positioned on smartwatch worn by the individual on a first extremity and a second electrode may be positioned on a wristlet worn by the individual on a second extremity. In this example, the first electrode on the smartwatch and the second electrode on the wristlet are both in communication with and controlled by the cardiac monitoring device.

In some embodiments, the devices described herein are configured to carry out machine learning. In some embodiments, the devices, systems, and methods described herein comprise machine learning algorithms which analyze parameter values sensed from an individual over period of time. In some embodiments, the devices, systems, and methods described herein comprise machine learning algorithms which analyze parameter values sensed from a plurality of individuals. In some embodiments, a machine learning algorithm causes the devices, systems, and methods described herein to more accurately identify or predict the presence of an arrhythmia in a given individual. For example, in some embodiments, sensed electrocardiogram data may be compared back to parameter values such as, for example, sensed heart rates and activity levels that triggered the sensing of said electrocardiograms. When, for example, sensed electrocardiograms confirm the presence of an arrhythmia, the presence of which was indicated by, for example, a discordance between other parameter values, the machine algorithm causes the device or system described herein to learn from that data. Similarly, when, for example, sensed electrocardiograms do not confirm the presence of an arrhythmia, the presence of which was indicated by, for example, a discordance between other parameter values, the machine algorithm causes the device or system described herein to learn from that data as well. That is, in some embodiments, the machine learning algorithm correlates the sensed electrocardiogram with the discordance between parameter values that caused it (i.e. the electrocardiogram) to be sensed. The presence or absence of an arrhythmia on the electrocardiogram either respectively reinforces the correlation of an arrhythmia with the discordance that caused the electrocardiogram to be sensed or contradicts the presence of a correlation of an arrhythmia with the discordance. For example, when a heart rate of 110 is sensed and simultaneously a resting activity is sensed, an electrocardiogram is caused to be sensed, and when the sensed electrocardiogram does not indicate a presence of an arrhythmia the machine learning algorithm causes the device or system as described herein to learn that for that individual a heart rate of 110 at rest does not necessarily indicate a presence of an arrhythmia. In some embodiments, the machine learning algorithm continues to cause the storing of parameter value data, such as, for example, heart rate, activity level, and heart rate variability, and compare the parameter values to the associated electrocardiogram data over time. Thus, in some embodiments, with multiple parameter values sensed over time and compared to associated electrocardiogram data, a cardiac monitoring device or system improves its ability to predict or identify the onset of arrhythmia based on a discordance between parameter values for a specific individual. In some embodiments, a machine learning algorithm may obviate the need to sense an electrocardiogram when a particular discordance is present between parameter values of a specific individual, because of an extremely high likelihood of a presence or absence of an arrhythmia based on the parameter values as determined by the machine learning algorithm.

Any of the devices, systems, and methods for cardiac monitoring described herein may comprise one or more of a smartphone, a laptop or desktop computer, a smartwatch, or a tablet computer.

Discordance Monitoring

Figure 7:
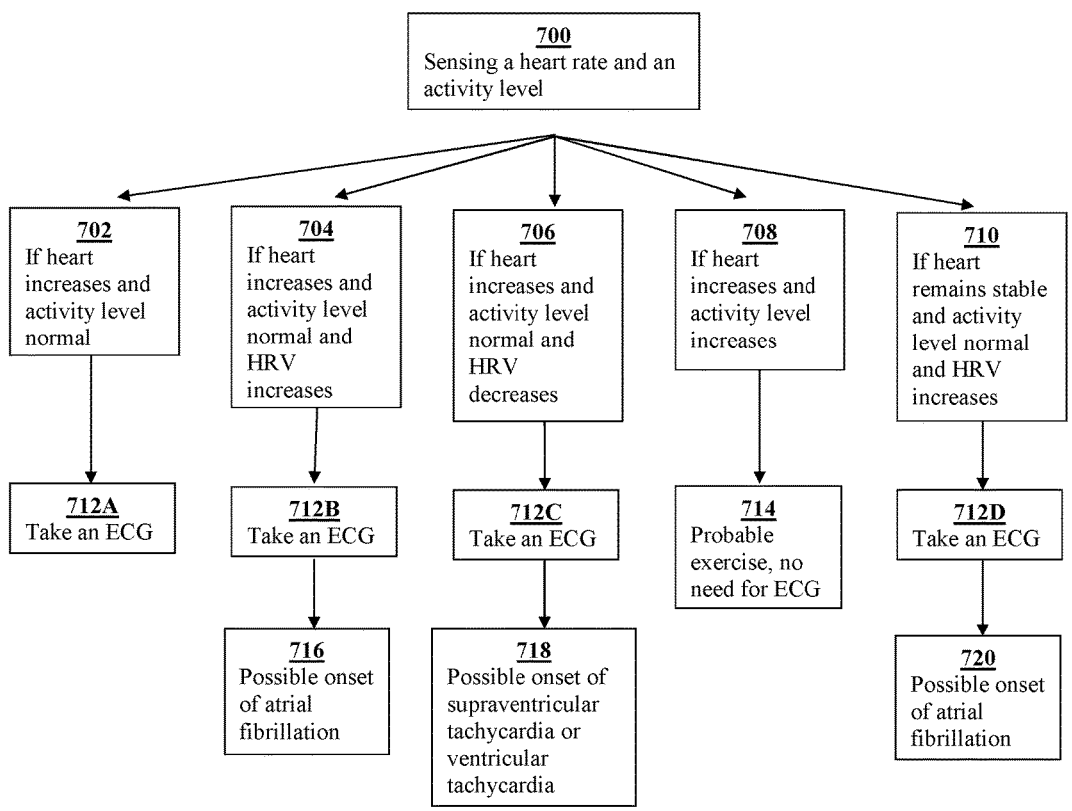
FIG. 7 shows a schematic of an algorithm for discordance monitoring.

FIG. 7 shows a schematic of an algorithm for discordance monitoring. In a step 700, a heart rate and an activity level are sensed by, for example, a device or system as described herein. In some embodiments, an activity level is sensed with a gyroscope or an accelerometer that is. Heart rate is sensed with a light based or other commonly used heart rate sensors. The device that measures the heart rate and the activity level may be the same device or more than one device. For example, a smartwatch or other wearable device may be configured to include a heart rate sensor as well as an activity level sensor.

If, as shown in a step 702, an increased heart rate is sensed together with a normal or resting activity level, the two values are determined to be in discordance by the device or system processor. That is, the elevated heart rate does no match the sensed stable activity level. Determination of the presence of the discordance is done by a processor of either the device or system as described herein. The identified discordance may indicate the presence of an arrhythmia. As such, an ECG is caused to be sensed in a step 712A. The step 712A, may, for example, comprise indicating to the user through the device or system that sensed the heart rate and activity level to contact one or more electrodes of an ECG sensing device and thus sense the ECG. The ECG sensing device may be the device or part of the system used to sense the heart rate and activity level or may be a separate device. For example, a user wearing a smartwatch with heart rate and activity level monitoring receives an audible and/or visual indication from the smartwatch to sense an ECG when a discordance is present between a sensed heart rate value and a sensed activity level value. In some embodiments, the smartwatch comprises one or more electrodes and a user contacts one electrode with the left side of their body and one electrode with the right side of their body when an indication is received to do so from the smartwatch because a discordance is present thus sensing an ECG. In some embodiments, a smartphone comprises one or more electrodes and a user contacts one electrode with the left side of their body and one electrode with the right side of their body when an indication is received to do so from the smartwatch because a discordance is present thus sensing an ECG.

If, as shown in step 704, an increased heart rate is sensed together with an increased heart rate variability, and a normal or resting activity level is sensed. The increased heart rate and HRV are in discordance with the normal or resting activity level, and a presence of a discordance is determined by the device or system processor. Once the discordance is determined, an ECG is caused to be sensed in a step 712B as, for example, described herein with respect to step 712A. As shown, in step 716, this particular discordance may be indicative of the presence of atrial fibrillation and it should be confirmed with the ECG 712B.

If, as shown in step 706, an increased heart rate is sensed together with a decreased heart rate variability and a normal or resting activity level is sensed. The increased heart rate, decreased heart rate variability, and normal or resting activity level are in discordance with each other, and a presence of a discordance is determined by the device or system processor. Once the discordance is determined, an ECG is caused to be sensed in a step 712C as, for example, described herein with respected to step 712A. As shown, in a step 718, supraventricular tachycardia may be present and it should be confirmed with the ECG of 712C.

If, as shown in a step 708, an increased heart rate is sensed together with an increased activity level, the device or system processor determines that no discordance is present, and an ECG is not recorded as the individual is probably exercising 714.

If, as shown in a step 710, a regular heart rate is sensed (e.g. 60-100 beats per minute) and an increased heart rate variability is sensed together with a normal or resting activity level. The normal heart rate, increased heart rate variability, and normal or resting activity level are in discordance with each other, and a presence of a discordance is determined by the device or system processor. Once the discordance is determined, an ECG is caused to be sensed in a step 712D as, for example, described herein with respect to step 712A. As shown, in a step 720, atrial fibrillation may be present and it should be confirmed with the ECG of 712D.

In some embodiments, a determination of the presence of a discordance is based on a comparison of two or more sensed physiologic parameters with each other. That is, for example, an elevated heart rate of 110 is compared to a resting activity level as sensed by an accelerometer which measures that the individual is traveling at 0 miles/hr. The 110 heart rate is elevated whereas the activity level of 0 miles/hr is a resting level, which indicates a discordance between the sensed heart rate and activity level. In some embodiments, a processor determines that the value of a sensed physiologic parameter is either above or below a threshold value or range of values. In some embodiments, the threshold value or range of values are deemed to be normal or resting values in the population. In some embodiments, the thresholds are specific to the biometric data of the user so that the user is, for example, age-matched or gender matched to the appropriate threshold from the general population. For example, an activity level is determined to be increased in a 70 year old user but would not be increased in a 7 year old user. Thus, a discordance is determined by qualifying if a sensed physiologic parameter is elevated, decreased, or normal (or resting) and then comparing that qualified value to a qualified value of another sensed physiologic parameter. That is, for example, a value that is qualified as either increased, decreased, or normal (or resting) is compared to a value that is also qualified as increased, decreased, or normal (or resting).

In some embodiments, there is the added step (not shown in FIG. 7) of the devices and systems described herein running machine learning algorithms so that the threshold values and ranges used to determine whether a sensed physiologic parameter is increased, decreased, normal (or resting) are adjusted to more accurately fit the user. That is, for example, a user who was determined, through ECG, to have an arrhythmia at a heart rate of 80 will have their heart rate threshold lowered so that a heart of 85 (which is normal in some) would be determined to be an increased rate. The machine learning algorithm more accurately sets the thresholds over time so that discordances are more accurately determined resulting in more accurate (and efficient) recording of ECGs in response to the determination of the presence of the discordance.

Table 1 below presents some of the information found in FIG. 7 in table form.

TABLE 1

| HR Data | Activity Level Data | HRV Data | Action |
|---|---|---|---|
| HR increases | Activity level stable | | Take an ECG, possible arrhythmia |
| HR increases | Activity level stable | HRV increases | Take an ECG, possible atrial fibrillation |
| HR increases | Activity level stable | HRV decreases | Take an ECG, possible supraventricular tachycardia or ventricular tachycardia |
| HR increases | Activity level increases | | Don't take an ECG, probable exercise |
| HR stable | Activity level stable | HRV increases | Take an ECG, possible atrial fibrillation |

While preferred embodiments of the present individual matter described herein have been shown and described herein, it will be obvious to those skilled in the art that such embodiments are provided by way of example only. Numerous variations, changes, and substitutions will now occur to those skilled in the art without departing from the individual matter described herein. It should be understood that various alternatives to the embodiments of the individual matter described herein described herein may be employed in practicing the individual matter described herein. It is intended that the following claims define the scope of the individual matter described herein and that methods and structures within the scope of these claims and their equivalents be covered thereby.

What is claimed is:

1. A computer-implemented system comprising:
a digital processing device comprising an activity level sensor configured to sense an activity level value and a heart rate sensor configured to sense a heart rate value;
a memory operatively coupled to the digital processing device, the memory device comprising executable instructions that cause the digital processing device to:
receive the activity level value that is measured by the activity level sensor and the heart rate value that is sensed by the heart rate sensor;
determine that a discordance is present between the activity level value and the heart rate value; and
apply, in response to determining that the discordance is present, a machine learning algorithm to determine that an arrhythmia is present.

2. The system of claim 1, wherein the digital processing device comprises a smartwatch.

3. The system of claim 1, wherein the digital processing device comprises a first electrode and a second electrode configured to sense an electrocardiogram.

4. The system of claim 1, wherein the machine learning algorithm is trained with data comprising an electrocardiogram showing the arrhythmia when the discordance is present.

5. The system of claim 3, wherein the digital processing device is further configured to determine a heart rate variability based on the heart rate value.

6. The system of claim 5, wherein the discordance is determined to be present between the activity level value and the heart rate value based on the heart rate variability value.

7. The system of claim 6, wherein the machine learning algorithm is configured to determine a presence of said arrhythmia on said electrocardiogram, and determine a correlation between the discordance and the arrhythmia when said arrhythmia is present on said electrocardiogram.

8. The system of claim 1, wherein the digital processing device is further configured to determine a duration of said arrhythmia.

9. A method for determining the presence of an arrhythmia, comprising:
sensing an activity level value of an individual with a first sensor of a digital processing device;
sensing a heart rate value of said individual with a second sensor of said digital processing device;
determining that a discordance is present between said activity level value and said heart rate value; and
applying, in response to determining that the discordance is present, a machine learning algorithm to determine that an arrhythmia is present.

10. The method of claim 9, wherein the digital processing device comprises a smartwatch.

11. The method of claim 9, wherein the digital processing device comprises a first electrode and a second electrode configured to sense an electrocardiogram.

12. The method of claim 10, wherein the machine learning algorithm is trained with data comprising an electrocardiogram showing the arrhythmia when the discordance is present.

13. The method of claim 11, further comprising determining a heart rate variability based on the heart rate value.

14. The method of claim 13, wherein the discordance is determined to be present between the activity level value and the heart rate value based on the heart rate variability value.

15. The method of claim 14, wherein the machine learning algorithm is configured to determine a presence of said arrhythmia on said electrocardiogram, and determine a correlation between the discordance and the arrhythmia when said arrhythmia is present on said electrocardiogram.

16. The method of claim 11, wherein the computer program comprises a software module configured to determine a duration of said arrhythmia.

* * * * *

UNITED STATES PATENT AND TRADEMARK OFFICE
CERTIFICATE OF CORRECTION

PATENT NO. : 10,537,250 B2
APPLICATION NO. : 15/656745
DATED : January 21, 2020
INVENTOR(S) : Albert et al.

It is certified that error appears in the above-identified patent and that said Letters Patent is hereby corrected as shown below:

On the Title Page

Item (72), add inventors:
--Omar Dawood, San Francisco, CA (US);
Ravi Gopalakrishnan, San Francisco, CA (US);
Fei Wang, San Francisco, CA (US);
Euan Thomson, Los Gatos, CA (US);
Iman Abuzeid, San Francisco, CA (US)--

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*